(12) United States Patent
Budakian et al.

(10) Patent No.: US 10,585,154 B1
(45) Date of Patent: Mar. 10, 2020

(54) NUCLEAR MAGNETIC RESONANCE DIFFRACTION

(71) Applicant: Quantum Valley Investment Fund LP, Waterloo (CA)

(72) Inventors: Raffi Ohannes Budakian, Waterloo (CA); Holger Haas, Kitchener (CA)

(73) Assignee: Quantum Valley Investment Fund LP, Waterloo (CA)

( * ) Notice: Subject to any disclaimer, the term of this patent is extended or adjusted under 35 U.S.C. 154(b) by 165 days.

(21) Appl. No.: 15/882,547

(22) Filed: Jan. 29, 2018

(51) Int. Cl.
| | | |
|---|---|---|
| G01R 33/385 | (2006.01) | |
| G01H 17/00 | (2006.01) | |
| G01N 24/08 | (2006.01) | |
| B82Y 10/00 | (2011.01) | |

(52) U.S. Cl.
CPC .......... G01R 33/385 (2013.01); G01H 17/00 (2013.01); G01N 24/08 (2013.01); B82Y 10/00 (2013.01)

(58) Field of Classification Search
CPC .............. G01R 33/385; G01R 33/3858; G01R 33/3456; G01R 33/34007; G01R 33/34; G01R 33/34092; G01R 33/345; G01R 33/38; G01R 33/44; G01R 33/46; G01N 2021/178; G01N 24/08; G01H 17/00; B82Y 10/00
USPC ............................. 324/76.49, 228, 300–322
See application file for complete search history.

(56) References Cited

U.S. PATENT DOCUMENTS

| | | | | |
|---|---|---|---|---|
| 5,266,913 A | * | 11/1993 | Chapman | G01R 33/4215 324/307 |
| 5,568,051 A | * | 10/1996 | Yamagata | G01R 33/385 324/318 |
| 5,610,521 A | * | 3/1997 | Zou | G01R 33/34 324/318 |
| 6,005,391 A | * | 12/1999 | Bornert | G01R 33/446 324/307 |
| 6,320,382 B1 | * | 11/2001 | Anderson | G01R 33/385 324/309 |
| 6,351,123 B1 | * | 2/2002 | Gebhardt | G01R 33/385 324/309 |
| 6,538,442 B2 | * | 3/2003 | Boskamp | G01R 33/4215 324/307 |

(Continued)

OTHER PUBLICATIONS

Budakian et al., Nanoscale Fourier-Transform Magnetic Resonance Imaging, Physical Review X-3 (2013). (Year: 2013).*

(Continued)

*Primary Examiner* — Patrick Assouad
*Assistant Examiner* — Sean Curtis
(74) *Attorney, Agent, or Firm* — Henry Patent Law Firm PLLC

(57) ABSTRACT

In a general aspect, a magnetic resonance system includes a primary magnet system configured to generate a principal magnetic field in a sample region. The magnetic resonance system also includes a field source device. The field source device includes a substrate and first and second conductor layers on the substrate. The first conductor layer includes a constriction configured to generate a radio frequency magnetic field in the sample region. The second conductor layer is vertically centered above the first conductor layer, and includes gradient coils configured to generate first, second, and third magnetic field gradients along respective first, second and third mutually-orthogonal spatial dimensions in the sample region.

24 Claims, 19 Drawing Sheets

(56) References Cited

U.S. PATENT DOCUMENTS

| | | | | |
|---|---|---|---|---|
| 6,798,200 | B2* | 9/2004 | Fan | B82Y 15/00 324/307 |
| 6,982,552 | B2* | 1/2006 | Hardy | G01R 33/385 324/307 |
| 7,034,533 | B2* | 4/2006 | Mugler, III | G01R 33/5613 324/309 |
| 7,436,180 | B2* | 10/2008 | Seeber | G01R 33/385 324/318 |
| 7,912,531 | B1* | 3/2011 | Chiu | A61B 5/055 324/309 |
| 8,698,496 | B2* | 4/2014 | Sorensen | G01R 33/4633 324/307 |
| 8,791,700 | B2* | 7/2014 | Witschey | G01R 33/445 324/307 |
| 9,360,542 | B2* | 6/2016 | Reeder | G01R 33/56563 |
| 9,581,670 | B2* | 2/2017 | Stemmer | G01R 33/56554 |
| 9,804,242 | B2* | 10/2017 | Hutter | G01R 33/56 |
| 9,841,484 | B2* | 12/2017 | Mohebbi | G01R 33/60 |
| 10,222,436 | B2* | 3/2019 | Yang | G01R 33/3858 |
| 10,238,329 | B2* | 3/2019 | Bansal | G01V 3/14 |
| 2009/0009169 | A1* | 1/2009 | Schulz | G01R 33/34046 324/318 |

OTHER PUBLICATIONS

Budakian et al., High-Resolution Nanoscale Solid-State Nuclear Magnetic Resonance Spectroscopy, Physical Review X-8 (2018). (Year: 2018).*

Budakian et al., Nanomechanical detection of nuclear magnetic resonance using a silicon nanowire oscillator, Physical Review B-85 (2012). (Year: 2012).*

Boutis , et al., "Pulse error compensating symmetric magic-echo trains", JMR (Journal of Magnetic Resonance) 161, Jun. 18, 2002, 6 pgs.

Boutis , et al., "Spin Diffusion of Correlated Two-Spin States in a Dielectric Crystal", Phys. Rev. L, vol. 92, No. 13, Apr. 2, 2004, 4 pgs.

Budakian, R. , "Nanowire-based magnetic resonance imaging and spectroscopy", presented to the Spin Mechanics 4 Conference, Feb. 20-25, 2017; Fairmont Chateau Lake Louise, Alberta, Canada, 40 pgs.

Budakian, R. , "Nanowire-based magnetic resonance imaging and spectroscopy", presented to the Institute for Quantum Computing on Jul. 8, 2017; Iqaluit, Nunavut, Canada, 42 pgs.

Budakian, R. , "Nanowire-based magnetic resonance imaging and spectroscopy", presented to the Rocky Mountain Conference on Magnetic Resonance, Jul. 17-21, 2016; Breckenridge, Colorado, USA, 49 pgs.

Chapman , et al., "Femtosecond X-ray protein nanocrystallography", Nature, vol. 470, Feb. 3, 2011, 6 pgs.

Dorner , et al., "Characterization of Protein Nanocrystals Based on the Reversibility of Crystallization", ACS Publications, American Chemical Society, May 2016, 8 pgs.

Falkner , et al., "Generation of Size-Controlled, Submicrometer Protein Crystals", Chem. Mater. vol. 17, No. 10, 2005, 8 pgs.

Mansfield , et al., ""Diffraction" and microscopy in solids and liquids by NMR", Physical Review B, vol. 12, No. 9, Nov. 1, 1975, 17 pgs.

Mansfield , et al., "NMR 'diffraction' in solids?", J. Phys. C: Solid State Phys. 6 L422, 1973, 6 pgs.

Nichol , et al., "Nanomechanical detection of nuclear magnetic resonance using a silicon nanowire oscillator", Phys. Rev. B 85, 054414, 2012, 6 pgs.

Nichol , et al., "Nanoscale Fourier-Transform Magnetic Resonance Imaging", Physical Review X 3, 031016, 2013, 7 pgs.

Rose , et al., "High-Resolution Nanoscale Solid-State Nuclear Magnetic Resonance Spectroscopy", arXiv:1707.01062v1, Jul. 4, 2017, 18 pgs.

Zhang , et al., "First Direct Measurement of the Spin Diffusion Rate in a Homogenous Solid", Phys. Rev. L., vol. 80, No. 6, Feb. 9, 1998, 4 pgs.

* cited by examiner

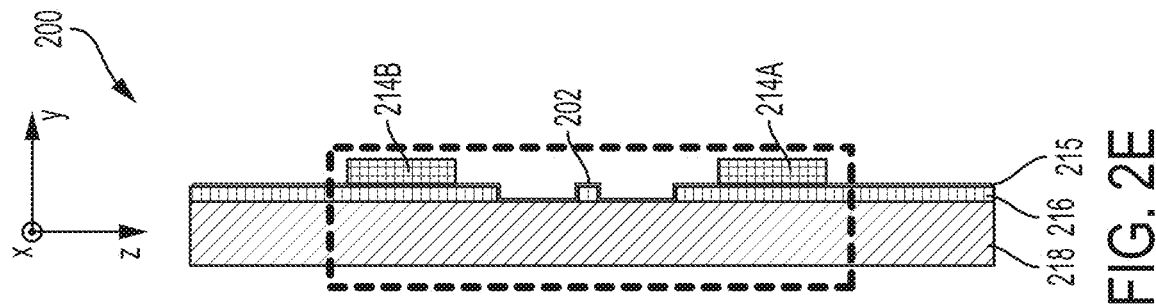
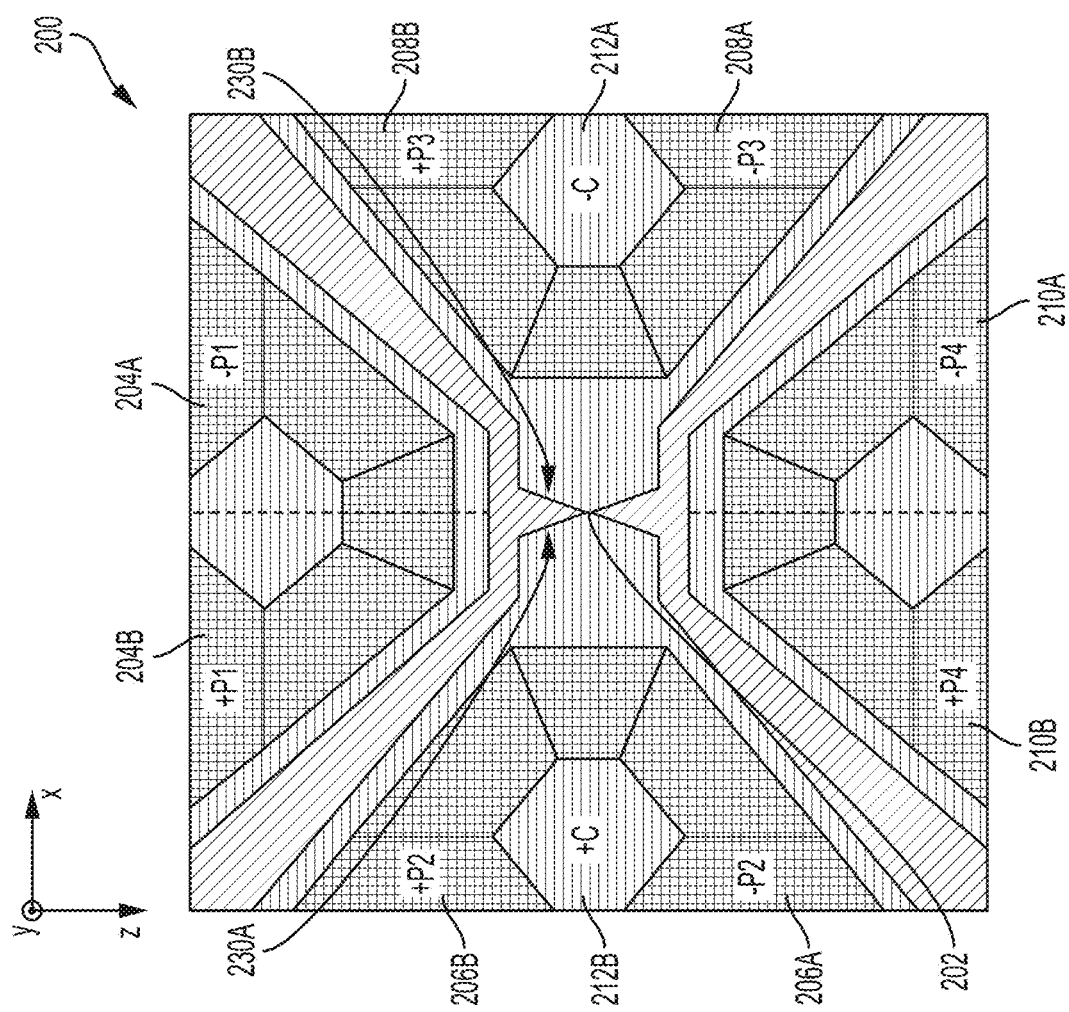

NUCLEAR MAGNETIC RESONANCE DIFFRACTION

BACKGROUND

The following description relates to nuclear magnetic resonance (NMR) diffraction.

Magnetic resonance systems are often used to study materials and material properties. For example, nuclear magnetic resonance (NMR) spectroscopy can be used to study molecular bonds and other properties of a material; and magnetic resonance imaging (MRI) can be used to generate three-dimensional images showing the structural properties of a material. Magnetic resonance systems typically use gradient fields and radio-frequency fields to manipulate the spins in a material, and to acquire magnetic resonance signals that can be processed to study the material.

DESCRIPTION OF DRAWINGS

FIGS. 2A, 2B, 2C, 2D, 2E, 2F and 2G include various side, perspective and cross-sectional views of an example magnetic field source device.

DETAILED DESCRIPTION

Figure 1A:
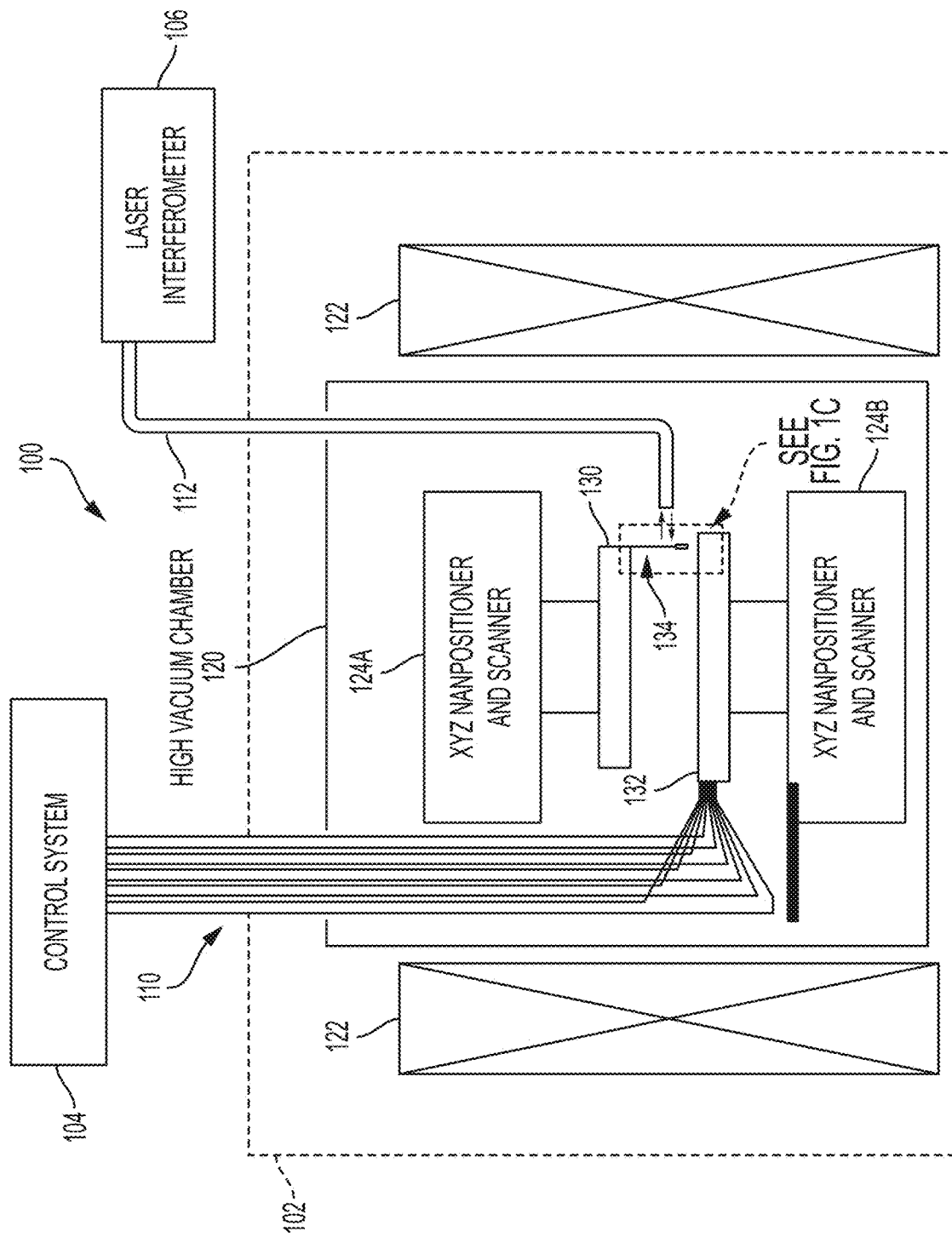
FIGS. 1A, 1B and 1C are schematic diagrams of an example magnetic resonance system.

In some aspects of what is described here, a magnetic resonance system includes a field source device that applies magnetic fields to a magnetic resonance sample. The field source device may be configured to apply gradient fields that vary (e.g., linearly) along three mutually-orthogonal spatial directions. The field source device may be configured to apply radio-frequency fields that coherently interact with spins in the sample. The field source device may be used to obtain atomic-scale resolution measurements of the sample. For example, the magnetic resonance system may obtain an NMR diffraction measurement having a resolution on the order of approximately 1 Angstrom (Å) to 10 Angstroms (Å), or a resolution in another range in some cases.

In some implementations, the magnetic resonance systems and techniques described here can be used to analyze the structure and dynamics of proteins or other types of microscopic structures. For instance, membrane proteins (MPs) are an important class of proteins; estimates indicate that MPs comprise 25-30% of proteins in all living species, and 40-60% of drug targets are MPs. The ability to achieve atomic resolution imaging and diffraction measurements can provide technical advantages and improvements when characterizing MPs and other types of structures. In some cases, diffraction measurements can be used to study biological structures, such as virus particles or cellular structures, including those that possess periodic structure on the nanometer or Angstrom scale.

Further, the magnetic resonance apparatus and techniques described here possess several important advantages over other techniques, such as high energy scattering probes (e.g. X-rays, electrons and neutrons), that are commonly used to study atomic structure. For example, magnetic resonance systems can use low frequency radiation that does not damage the structures being studied. This is particularly important for biological materials, that may be easily damaged by high energy probes, such as X-rays and electrons. Additionally, NMR diffraction may be chemically selective, thus offering greater structural information as compared to most scattering probes that only probe electron density (and in turn provide limited information about the chemical composition). In addition, magnetic resonance systems typically are highly sensitive to hydrogen, which is invisible to X-rays. This consideration is particularly important for imaging biomolecules, where hydrogen is the primary constituent.

In some implementations, the magnetic resonance apparatus and techniques described here can be used in a force-detected magnetic resonance (FDMR) system. For instance, the magnetic resonance apparatus and techniques described here may be used to improve or otherwise modify existing FDMR systems such as the FDMR paradigm described in the publication "Nanoscale Fourier Transform Magnetic Resonance Imaging," Physical Review X, 3, 031016, published in September 2013, or another type of FDMR system. When considering the application of NMR diffraction to determine the structure of proteins, an FDMR system can combine high spin detection sensitivity (e.g., of a nanowire-based magnetic resonance detection) with NMR diffraction to measure the structure of proteins and other biologically-relevant macromolecular assemblies using nanocrystalline samples.

In some implementations, the magnetic resonance apparatus and techniques described here can be used in optically-detected magnetic resonance (ODMR) systems. For instance, the magnetic resonance apparatus and techniques described here may be used to improve or otherwise modify existing ODMR systems such as those used to study NV centers in diamond crystals, or another type of ODMR system.

Figure 1B:
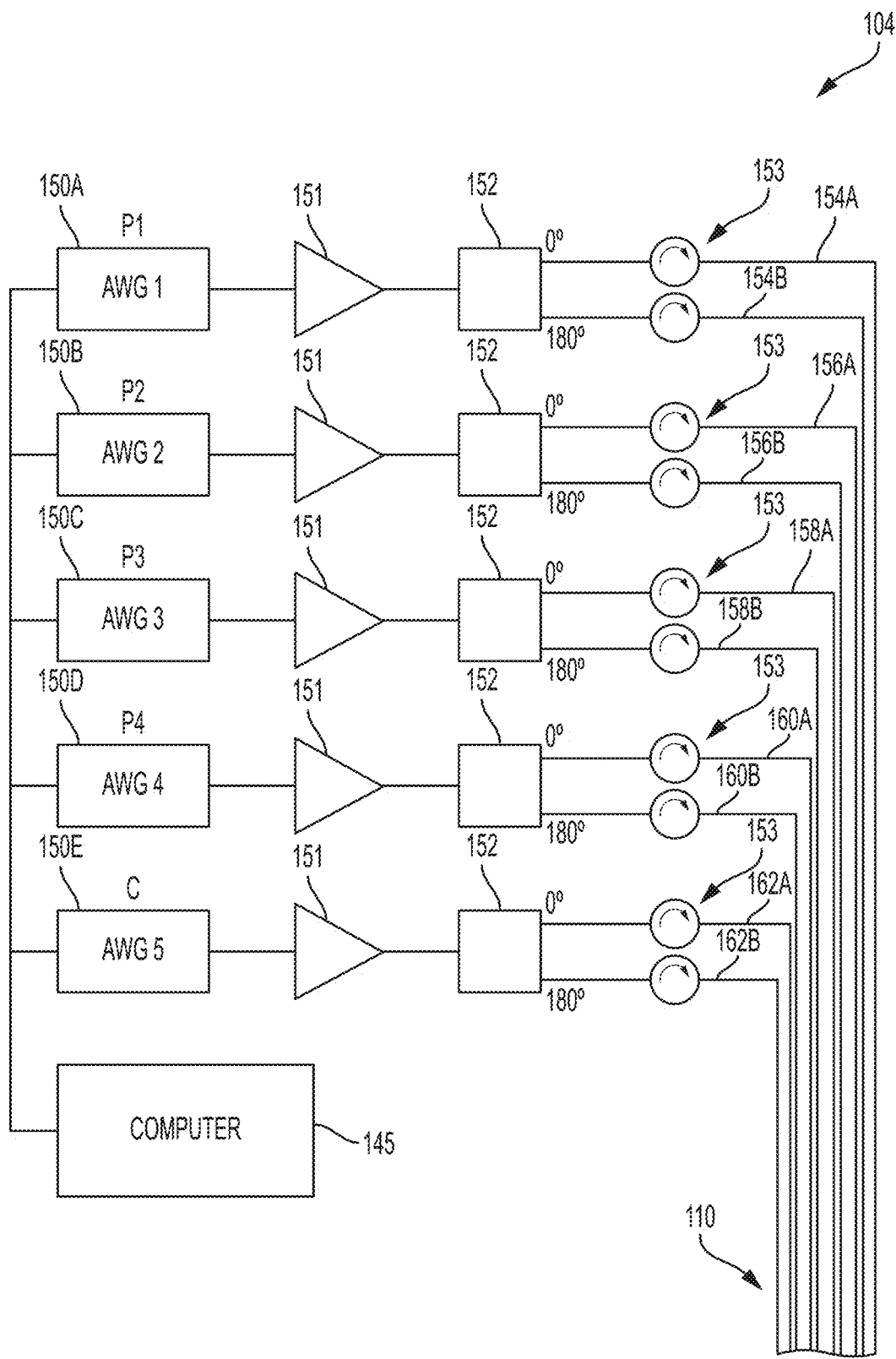
Figure 1C:
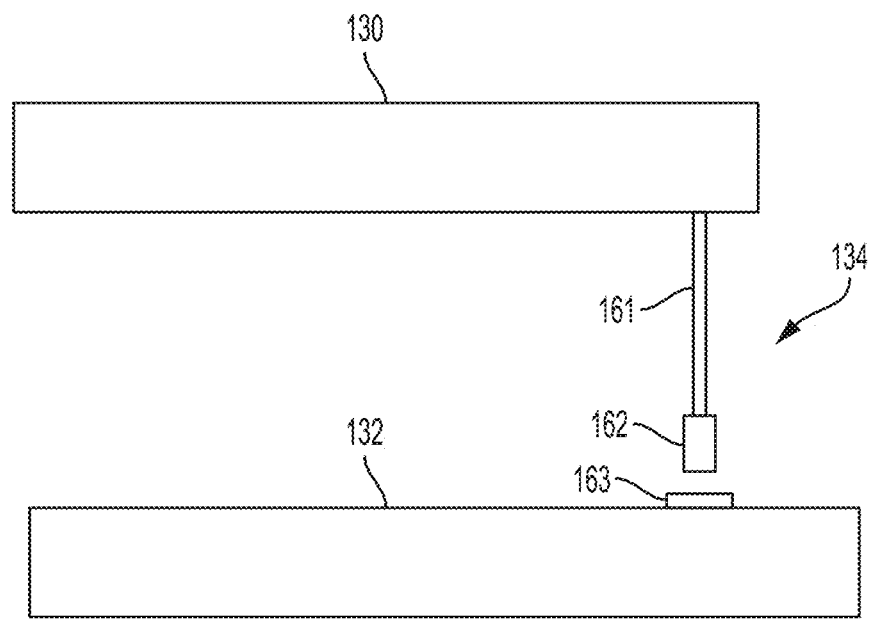

FIGS. 1A, 1B and 1C are schematic diagrams of an example magnetic resonance system 100. As shown in FIG. 1A, the magnetic resonance system 100 includes a high vacuum chamber 120, positioned in a magnetic field generated by a superconducting magnet system 122. The superconducting magnet system 122 can operate as a primary magnet system that generates a principal magnetic field in a sample region (sometimes referred to as the primary or quantizing magnetic field). As shown in FIGS. 1A and 1C, a magnetic resonance sample 162 in a central region 134 of the vacuum chamber 120 is subject to the principal magnetic field, and the principal magnetic field polarizes nuclear spins in the magnetic resonance sample 162. The strength of the principal magnetic field, along with the gyromagnetic ratio of the spins, determines the resonance frequency of the spins in magnetic resonance sample 162. In some examples, the magnetic resonance sample 162 is a nanocrystal material or another type of material.

The magnetic resonance system 100 also includes nanopositioners and scanners 124A and 124B that control the three-dimensional spatial positions of elements in the central region 134. A first nano-positioner and scanner 124A controls the position of a first support element 130, and a second nano-positioner and scanner 124B controls the position of a second support element 132. In the example shown, the first support element 130 is a silicon substrate, and the second support element 132 is a sapphire substrate. The support elements may include other types of materials and structures, including other types of substrates.

As shown in FIG. 1C, the first support element 130 supports a cantilever 161 that holds the magnetic resonance sample 162. In the example shown, the cantilever 161 is a silicon nanowire, which is a mechanical resonator that is mechanically coupled to the sample 162. The second support element 132 supports a field source device 163. The field source device 163 is positioned below the magnetic resonance sample 162.

Figure 2A:
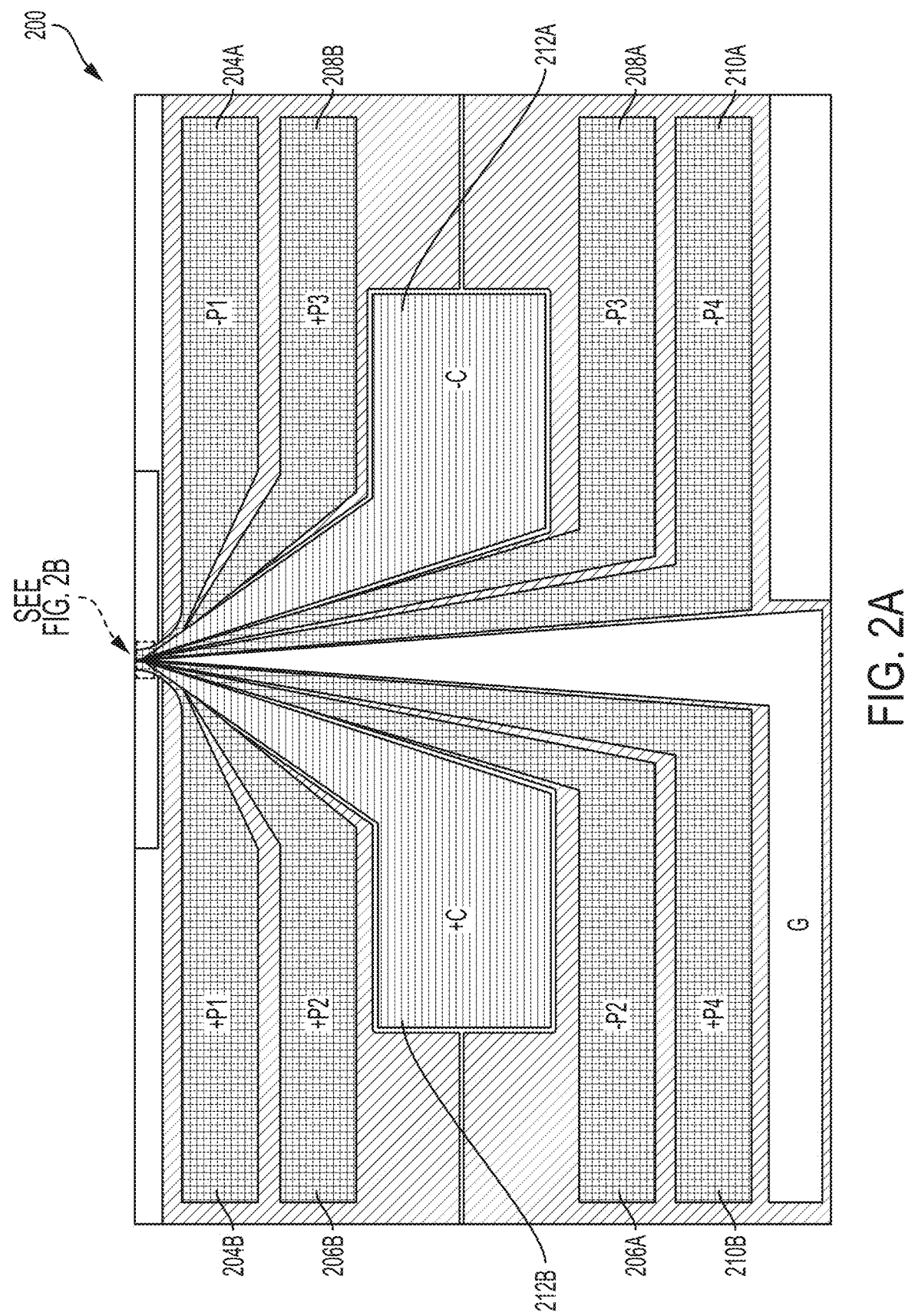
Figure 2B:
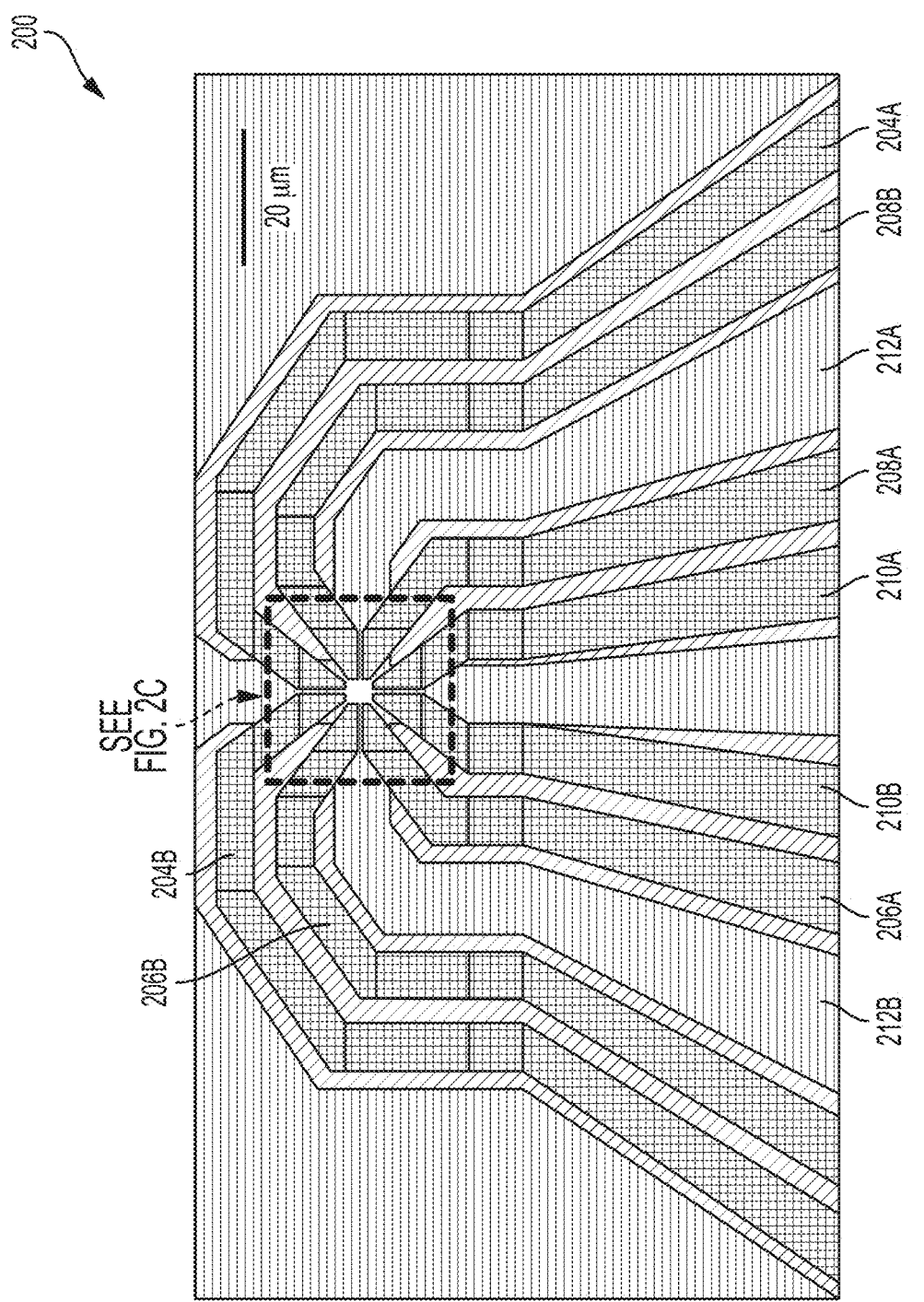
Figure 2C:
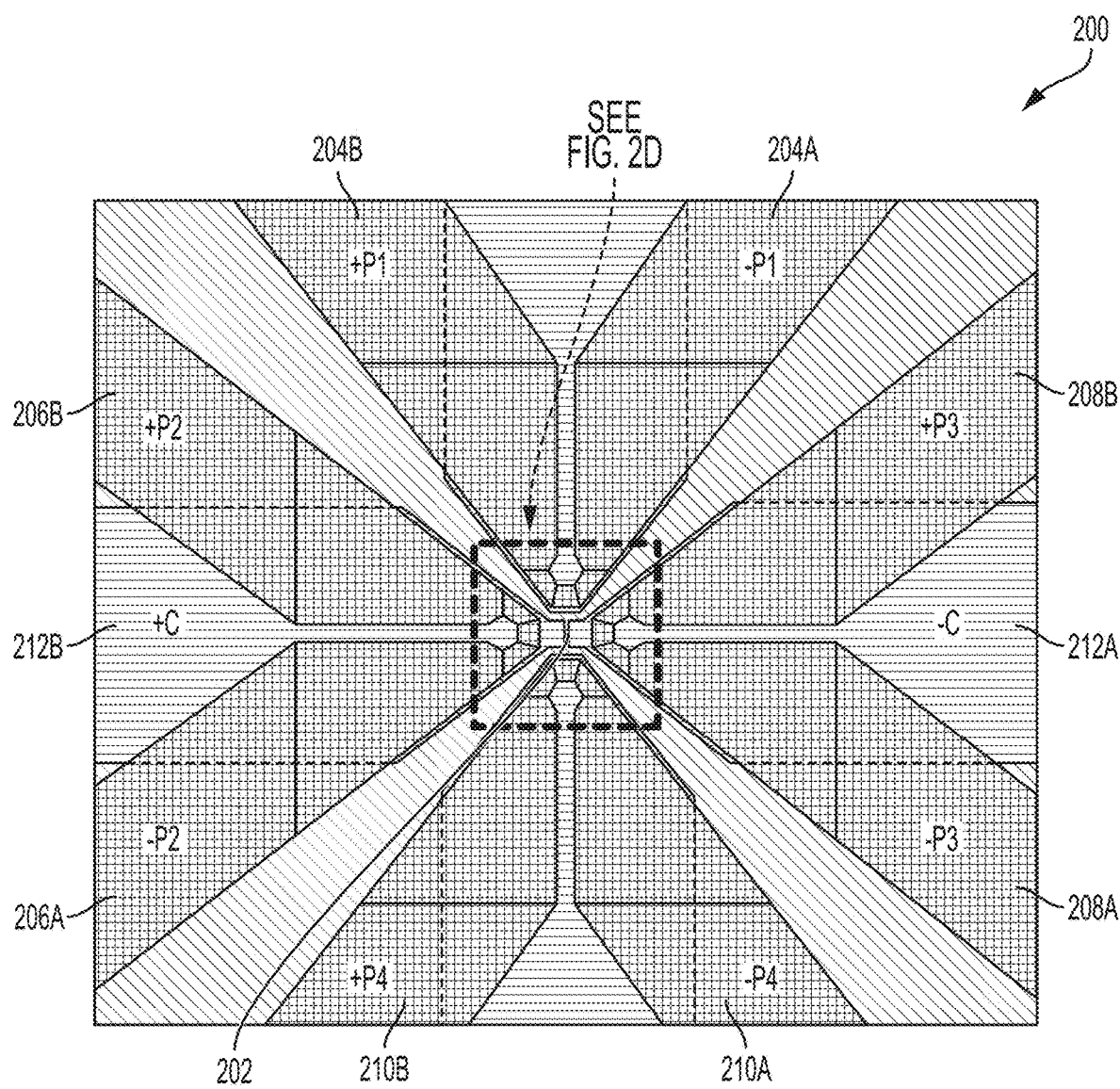
Figure 2F:
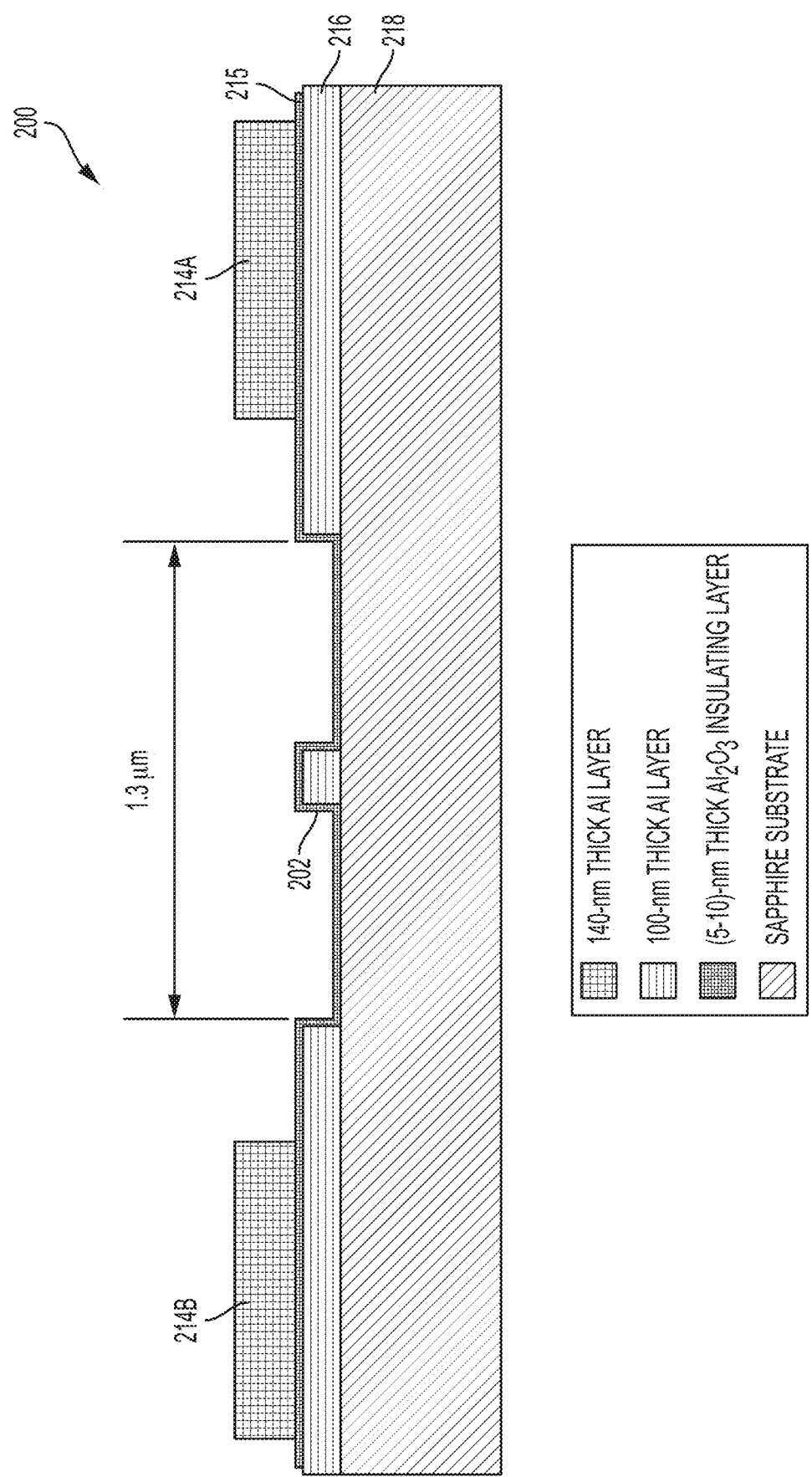
Figure 2G:
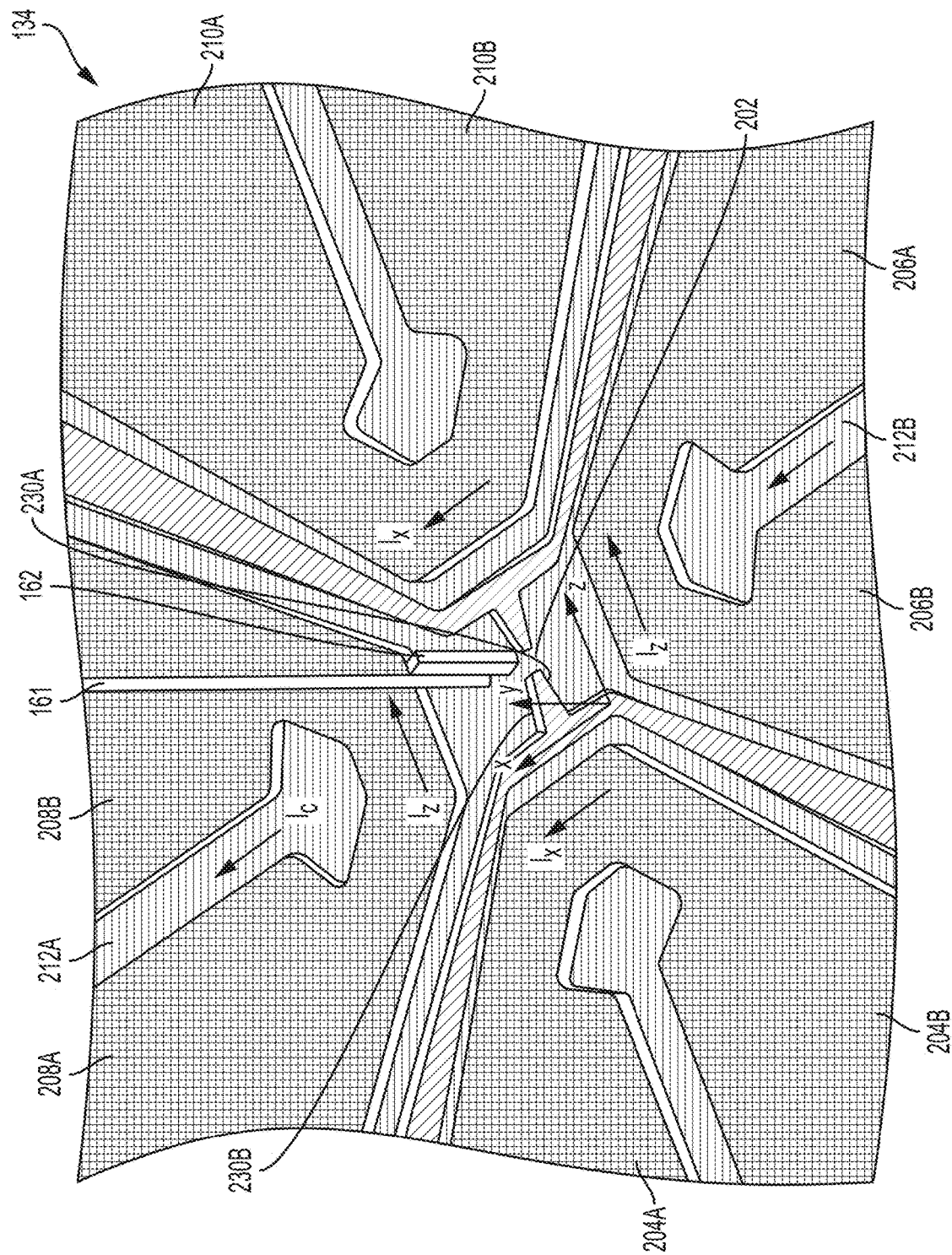
Figure 3A:
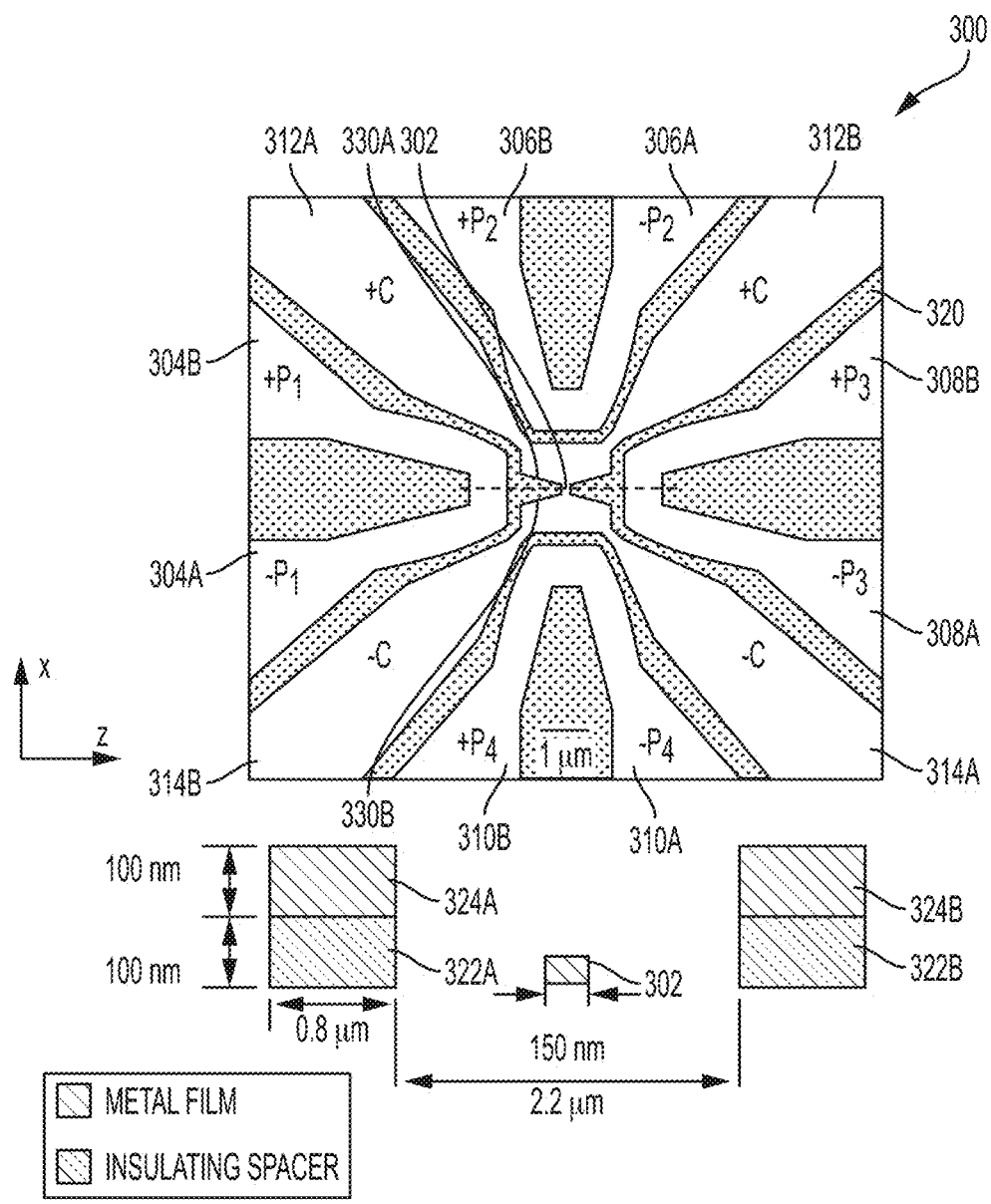
FIGS. 3A and 3B include various perspective, side and cross-sectional views of another example magnetic field source device.
Figure 3B:
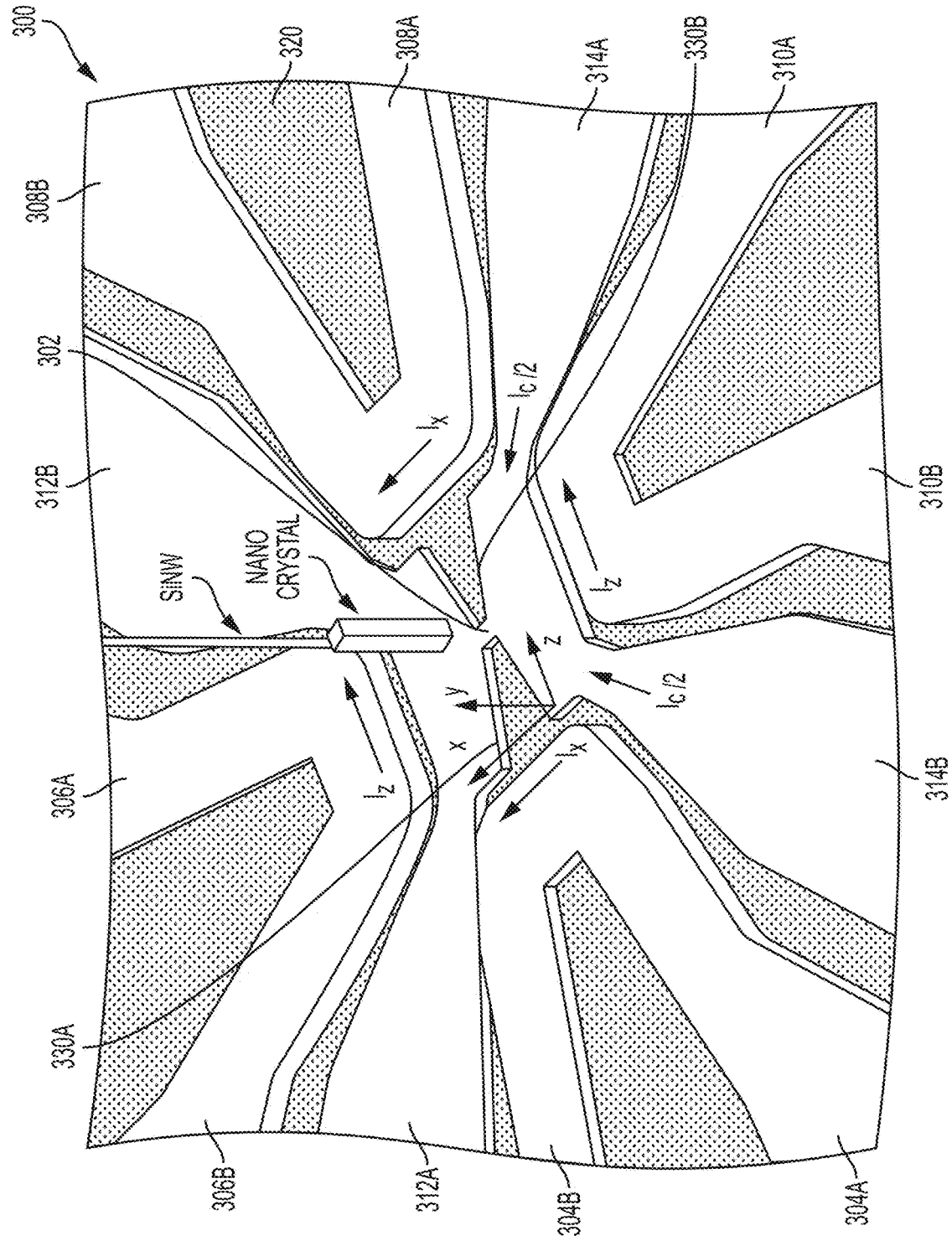

The field source device 163 can be implemented using the example field source device 200 shown in FIGS. 2A-2G, the example field source device 300 shown in FIGS. 3A-3B, or another type of field source device. In some instances, the field source device 163 applies magnetic field gradients across the magnetic resonance sample 162 to generate a coherent spatial encoding of the spins, and applies radio-frequency magnetic fields to coherently manipulate the spins in the magnetic resonance sample 162. For example, the field source device 163 may generate magnetic field gradients of the type shown in FIGS. 4A, 4B, 4C, 5A, and 5B and apply pulse sequences of the type shown in FIG. 6. The field source device 163 may apply other types of magnetic field gradients and pulse sequences in some cases.

The magnetic resonance system 100 shown in FIG. 1A is an example of a force-detected magnetic resonance (FDMR) system. To obtain a magnetic resonance signal, a laser interferometer 106 monitors movements and displacements of the cantilever 161 based on optical signals obtained via optical fiber 112. A readout pulse sequence applied to the magnetic resonance sample 162 by the field source device 163 can induce the movement and displacement of the cantilever 161 via mechanical coupling between the cantilever 161 and the magnetic resonance sample 162. For example, magnetic field pulses applied to the nuclear spins in the magnetic resonance sample 132 can generate an oscillating magnetic force acting on the cantilever 131. To resonantly excite the cantilever 131, the magnetic moments of the nuclear spins can be manipulated at or near the cantilever's mechanical resonance frequency.

The mechanical oscillations of the cantilever 131 can be measured, for example, by an optical interferometer, beam deflection detector or another type of optical sensor system. In the example shown in FIG. 1A, the laser interferometer 106 produces a signal that is proportional to the cantilever oscillation amplitude, which depends on the magnetic moments of the nuclear spins in the magnetic resonance sample 162. Accordingly, movement and oscillations of the cantilever 161 may be used to measure attributes of the magnetic resonance sample 162. The spatial resolution of such measurements is determined, at least in part, by the spatial resolution of the coherent spatial encoding of the spins, which is generated by magnetic field gradients produced by the field source device 163.

The magnetic resonance system 100 also includes a control system 104, shown in FIGS. 1A and 1B, which is operably connected to the field source device 163. Each of the arbitrary waveform generators (AWGs) 150A, 150B, 150C, 150D, 150E shown in FIG. 1B can be operated to synthesize magnetic resonance control signals that are delivered to the field source device 163 and cause the field source device 163 to apply magnetic fields to the magnetic resonance sample 162. In the example shown in FIG. 1B, four of the AWGs 150A, 150B, 150C, 150D generate respective waveforms (P1, P2, P3, P4) that are delivered to gradient coils in the field source device 163 (e.g., the four outer gradient wires of the example field source device 200 shown in FIGS. 2A, 2B, 2C, 2D, 2E, 2F, 2G, the four outer gradient wires of the example field source device 300 shown in FIGS. 3A, 3B, or another type of gradient coil). The fifth AWG 150E is used to synthesize radio-frequency waveforms (C) that are delivered to a radio-frequency coil in the field source device 163 (e.g., the constriction 202 shown in FIGS. 2F and 2G, the constriction 302 shown in FIGS. 3A and 3B, or another type of radio-frequency coil).

The waveforms may be synthesized on a computer 145 and communicated to the AWGs 150A, 150B, 150C, 150D, 150C, 150E. The output of each AWG is amplified by a respective on of the amplifiers 151 and passed through a phase splitter 152 that produces a differential voltage across a respective pair of conducting leads. The two output leads from each phase splitter 152 are connected through an isolator 153 for impedance matching. The signals from each of the (AWGs) 150A, 150B, 150C, 150D, 150E, after being processed by the control system electronics, are sent through electromagnetic connections 110 (e.g., coaxial cables, waveguides, or other types of connections) to the field source device 163 in the vacuum chamber 120.

The lithographic layout of an example field source device 200 is shown in FIG. 2A. FIGS. 2B, 2C, and 2D show successive zoomed-in views of the radio-frequency coil and four gradient coils in the example field source device 200. FIG. 2B shows a zoomed-in view of the region labeled in FIG. 2A. Similarly, FIG. 2C shows a zoomed-in view of the region labeled in FIG. 2B. And FIG. 2D shows a zoomed-in view of the region labeled in FIG. 2C. FIG. 2E shows a cross-sectional side view of the example field source device 200, taken along the dashed line in FIG. 2D. FIG. 2F shows a zoomed-in view of the region labeled in FIG. 2E. The example field source device 200 may be deployed as the field source device 163 in the magnetic resonance system 100 or another type of magnetic resonance system. FIG. 2G shows a perspective view of the example field source device 200 below the cantilever 161 and magnetic resonance sample 162 from FIG. 1C.

When the example field source device 200 is deployed in the magnetic resonance system 100, each of the leads shown in FIG. 2A can be electrically connected to a respective one of the leads in FIG. 1B to receive the waveforms generated by the AWGs in FIG. 1B. In FIGS. 2A, 2B, 2C, 2D, 2E, 2F and 2G, the label on each respective lead indicates which waveform (P1, P2, P3 or P4) is received by the lead, and the "+" or "−" label refers to the 0° or 180° output of the splitter that produces the associated signals. For example, terminal 154A in FIG. 1B can be connected to terminal 204A (−P1) in FIG. 2A, and terminal 154B in FIG. 1B can be connected to terminal 204B (+P1) in FIG. 2A. Similarly, terminal 156A in FIG. 1B can be connected to terminal 206A (−P2) in FIG. 2A, and terminal 156B in FIG. 1B can be connected to terminal 206B (+P2) in FIG. 2A. Similarly, terminal 158A in FIG. 1B can be connected to terminal 208A (−P3) in FIG. 2A, and terminal 158B in FIG. 1B can be connected to terminal 208B (+P3) in FIG. 2A. Similarly, terminal 160A in FIG. 1B can be connected to terminal 210A (−P4) in FIG. 2A, and terminal 160B in FIG. 1B can be connected to terminal 210B (+P4) in FIG. 2A. Finally, terminal 162A in FIG. 1B can be connected to terminal 212A in FIG. 2A (−C), and terminal 162B in FIG. 1B can be connected to terminal 212B (+C) in FIG. 2A. The terminals can be connected in another manner in some cases.

In some aspects of operation, the terminals 204A, 204B, 206A, 206B, 208A, 208B, 210A and 210B that form the gradient coils receive respective current waveforms (P1, P2, P3, P4) to produce magnetic field gradients within the sample volume. Similarly, the terminals 212A and 212B receive current waveforms (C) that are passed through the constriction 202 to generate radio-frequency magnetic fields within the sample volume.

As shown in the cross-sectional views in FIGS. 2E and 2F, the example field source device 200 includes a substrate 218, a conductor layer 216 and a gradient wire layer 214A, 214B. The substrate 218 can be, for example, a silicon substrate, a sapphire substrate or another type of substrate. In some examples, the conductor layer 216 is an aluminum layer having a thickness in the range of 100 nm to 200 nm; or the conductor layer 216 can be another material or thickness. The conductor layer 216 includes the constriction 202, the tapered portions 230A, 230B and the terminals 212A, 212B shown in FIG. 2D. In some examples, the constriction 202 is 150 nm wide at its narrowest point. In some examples, the constriction 202 may have a maximum width in the range of 150 to 300 nanometers (nm). An insulating layer 215 is located between the conductor layer 216 and the gradient wire layer 214A, 214B. In some examples, the insulating layer 215 is an aluminum oxide ($Al_2O_3$) layer having a thickness between 5 nm and 10 nm; or the insulating layer 215 can be another material or thickness. The gradient wire layer 214A, 214B is located above the insulating layer 215. The gradient wire layer 214A, 214B includes the terminals 204A, 204B, 206A, 206B, 208A, 208B, 210A and 210B that form the gradient coils. In some examples, the gradient wire layer 214A, 214B is an aluminum layer having a thickness in the range of 100 nm to 200 nm; or the gradient wire layer 214A, 214B can be another material or thickness.

The example field source device 200 may be fabricated by depositing a uniform-thickness (e.g., 100 nm) aluminum (Al) film on the substrate 218. The conductor layer 216, which contains the constriction 202, may be patterned using electron beam (e-beam) lithography and reactive ion etched to define the Al features shown in FIGS. 2A-2F. Next, a 5-10 nm thick $Al_2O_3$ layer can be deposited by atomic layer deposition to form the insulating layer 215, which electrically insulates between the conductor layer 216 and the gradient wire layer 214A, 214B. The gradient wire layer 214A, 214B may be patterned by e-beam lithography above the insulating layer 215. An e-beam evaporation and liftoff processes may be used to fabricate the gradient wire layer 214A, 214B.

A portion of the conductor layer 216 below the gradient wire layer 214A, 214B may function as a spacer to vertically offset the gradient coils above the top surface of the constriction 202. For example, during operation, the magnetic resonance sample can be located in the sample region above the constriction 202 in the vertical center of the gradient wire layer 214A, 214B. This placement may enable the application of highly-uniform magnetic field gradients necessary for minimizing phase variation over the magnetic resonance sample. The high uniformity can maximize the coherent volume of spins contributing to the magnetic resonance signal.

In the example shown in FIG. 2G, the magnetic resonance sample 162 is mechanically attached to the cantilever 161 and placed above constriction 202 of the field source device 200. Magnetic field gradients may be produced by flowing current pairwise through gradient coils on opposite sides of the sample region. The currents $I_z$ carried in the z-direction by a first pair of gradient coils (the gradient coil formed by the terminals 208A, 208B; and the gradient coil formed by the terminals 206A, 206B) produce a linear magnetic field gradient along the x-direction. The currents $I_x$ carried in the x-direction by a second pair of gradient coils (the gradient coil formed by the terminals 210A, 210B; and the gradient coil formed by the terminals 204A, 204B) produce a linear magnetic field gradient along the z-direction. A linear magnetic field gradient can be produced along the y-direction by using currents through all four gradient coils to generate magnetic field that rotates about the y-axis. The magnetic fields gradients can be used to produce high resolution imaging of the magnetic resonance sample 162. The current labeled $I_c$ flows through the constriction 202 and generates radio-frequency magnetic fields.

As shown in FIGS. 2D and 2G, the conductor in the conductor layer 216 on the substrate 218 includes two tapered portions 230A, 230B that are tapered in opposite directions parallel to the surface of the substrate 218. The first tapered portion 230A is tapered in the +x direction, and the second tapered portion 230B is tapered in the −x direction. The constriction 202 connects the respective narrow ends of the two tapered portions 230A, 230B. The field source device 200 also includes gradient coils in the gradient coil layer 214A, 214B on the substrate. A first gradient coil is formed by terminals 204A, 204B, a second gradient coil is formed by terminals 206A, 206B, a third gradient coil is formed by terminals 208A, 208B, and a fourth gradient coil is formed by terminals 210A, 210B. The gradient coils are spaced apart from the substrate (in the y-direction), and the vertical thickness (in the y-direction) of the gradient coils is centered, in a direction perpendicular to the surface (the y-direction), above a maximum height of the constriction 202, as shown in FIGS. 2E, 2F and 2G.

Pairs of the gradient coils are positioned opposite one another as shown in FIG. 2G. For example, the first gradient coil (formed by terminals 204A, 204B) and the fourth gradient coil (formed by terminals 210A, 210B) form a first pair that each carry the current $I_x$; and the second gradient coil (formed by terminals 206A, 206B) and the third gradient coil (formed by terminals 208A, 208B) form a second pair that each carry the current $I_z$. In some instances, the first pair of gradient coils is configured to generate a first magnetic field gradient, in the sample region, along a first spatial dimension (e.g., the z-dimension) parallel to the surface, and the second pair of gradient coils is configured to generate a second magnetic field gradient, in the sample region, along a second spatial dimension (e.g., the x-dimension) parallel to the surface. Both pairs of gradient coils may be used together to generate a third (rotating) magnetic field gradient, in the sample region, along a third spatial dimension (e.g., the y-dimension). The constriction 202 is configured to generate radio-frequency pulses in the sample region, including a readout magnetic field gradient along the third spatial dimension (the y-dimension) perpendicular to the surface of the substrate 218.

FIGS. 3A and 3B show another example field source device 300. The example field source device 300 may be fabricated by e-beam patterning a high conductivity metal (e.g., aluminum, silver, copper, or gold) on a substrate 320 to form the current-carrying pathways shown as conductors 304A, 304B, 306A, 306B, 308A, 308B, 310A, 310B. Dimensions for an example implementation are shown in FIG. 3A. Other shapes, dimensions and materials may be used in some implementations.

When the example field source device 300 is deployed in the magnetic resonance system 100, each of the conductors shown in FIG. 3A can be electrically connected to a respective one of the leads in FIG. 1B to receive the waveforms generated by the AWGs in FIG. 1B. In FIGS. 3A, 3B, the spin label on each respective lead indicates which waveform (P1, P2, P3 or P4) is received by the lead, and the "+" or "−" label refers to the 0° or 180° output of the splitter that produces the associated signals. For example, terminal 154A in FIG. 1B can be connected to terminal 304A (−P1) in FIG. 3A, and terminal 154B in FIG. 1B can be connected to terminal 304B (+P1) in FIG. 3A. Similarly, terminal 156A in FIG. 1B can be connected to terminal 306A (−P2) in FIG. 3A, and terminal 156B in FIG. 1B can be connected to terminal 306B (+P2) in FIG. 3A. Similarly, terminal 158A in FIG. 1B can be connected to terminal 308A (−P3) in FIG. 3A, and terminal 158B in FIG. 1B can be connected to terminal 308B (+P3) in FIG. 3A. Similarly, terminal 160A in FIG. 1B can be connected to terminal 310A (−P4) in FIG. 3A, and terminal 160B in FIG. 1B can be connected to terminal 310B (+P4) in FIG. 3A. Finally, terminal 162A in FIG. 1B can be connected to terminals 312A, 312B in FIG. 3A (+C), and terminal 162B in FIG. 1B can be connected to terminals 314A, 314B (1C) in FIG. 3A. The terminals can be connected in another manner in some cases.

As shown in the cross-section view in FIG. 3A (taken along the dashed line in FIG. 3A), the field source device 300 includes an insulator layer 322A, 322B, and one or more conductor layers that include the constriction 302 and gradient coils. A conductor layer on the substrate 320 includes two tapered portions 330A, 330B that are tapered in opposite directions parallel to the surface of the substrate 320. The first tapered portion 330A is tapered in the +x direction, and the second tapered portion 330B is tapered in the −x direction. The constriction 302 connects the respective narrow ends of the two tapered portions 330A, 330B. A conductor layer on the substrate 320 includes gradient coils 324A, 324B that are spaced apart from the substrate (in the y-direction) by the insulator layer 322A, 322B. In the example shown, the vertical thickness (in the y-direction) of the gradient coils is centered, in a direction perpendicular to the surface (the y-direction), above a maximum height of the constriction 302, as shown in FIG. 3A.

The example field source device 300 can operate similar to the operation of the field source device 200 described above. In the example shown in FIG. 3B, the magnetic resonance sample 162 is mechanically attached to the cantilever 161 and placed above constriction 302 of the field source device 300. Magnetic field gradients may be produced in the sample region by flowing current pairwise through gradient coils on opposite sides of the sample region. The currents $I_z$ carried in the z-direction by a first pair of gradient coils in FIG. 3B produce a linear magnetic field gradient along the x-direction. The currents $I_x$ carried in the x-direction by a second pair of gradient coils in FIG. 3B produce a linear magnetic field gradient along the z-direction. A linear magnetic field gradient can be produced along the y-direction by using currents through all four gradient coils in FIG. 3B to generate magnetic field that rotates about the y-axis. The magnetic fields gradients can be used to produce high resolution imaging of the magnetic resonance sample 162. The current labeled $I_c$ flows through the constriction 302 and generates radio-frequency magnetic fields.

In some implementations, a field source device (e.g., the field source device 163 shown in FIG. 1C, the field source device 200 shown in FIGS. 2A-2G, the field source device 300 shown in FIGS. 3A-3B, or another field source device) is used for atomic-scale nuclear magnetic resonance (NMR) diffraction. To facilitate understanding of NMR diffraction, consider a displacement vector R that defines the periodic arrangement of atoms in a nanocrystal. The displacement vector R may be associated with a particular element, spin species or other atomic-scale element having a distinct magnetic resonance frequency. The displacement vector R may be represented as follows:

$$R = n_1 a_1 + n_2 a_2 + n_3 a_3,$$

where $a_i$ are the primitive cell basis vectors, and $n_i \in \mathbb{Z}$. To encode a phase on the spin distribution, a static (principal) magnetic field is applied, and the spin coherence is evolved under a set of linear magnetic field gradients. The phase encoding generated by the magnetic field gradients is a coherent spatial encoding of the spins that can be used to obtain NMR diffraction measurements.

Figure 4A:
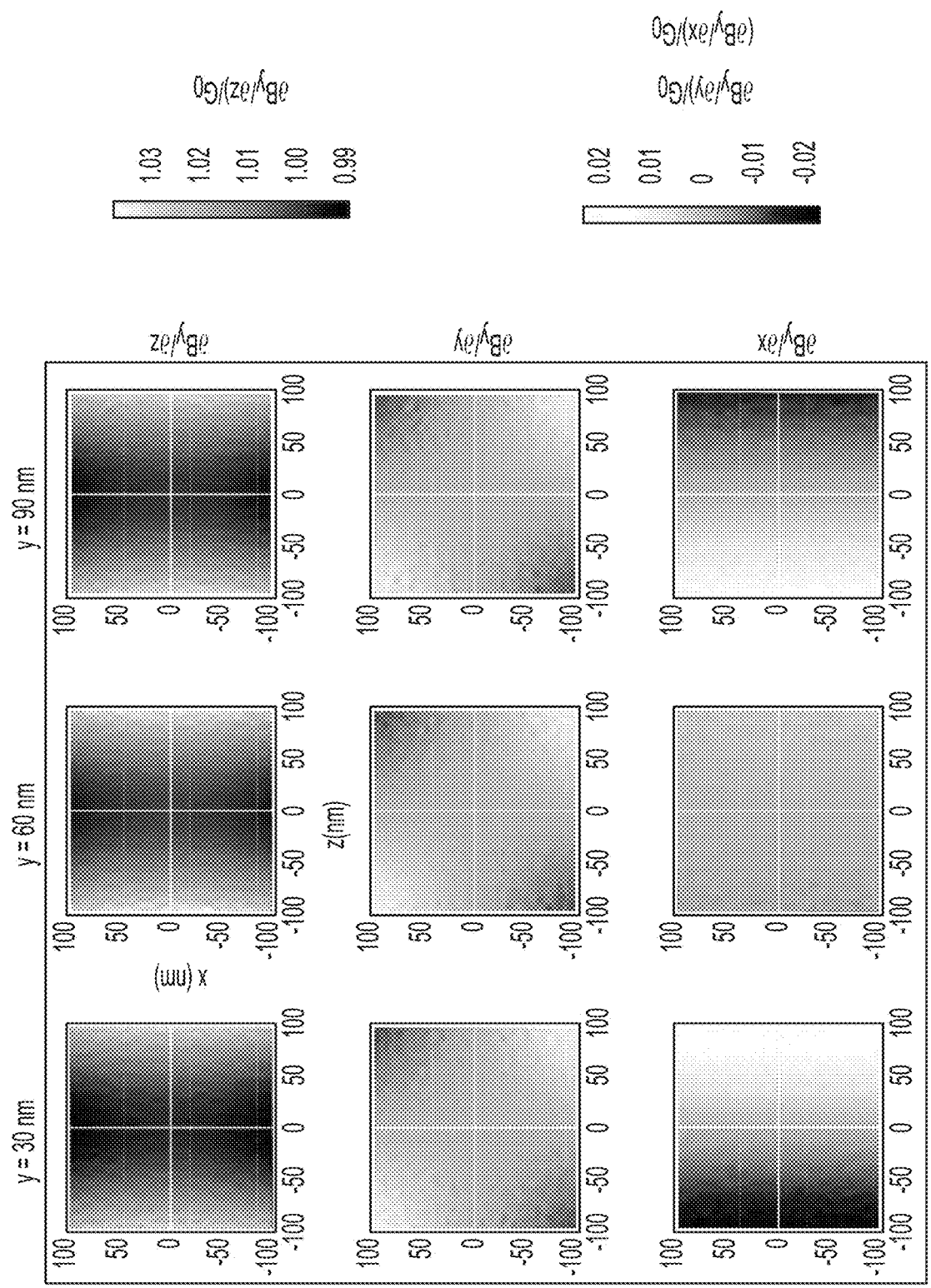
FIGS. 4A, 4B and 4C include a collection of plots showing numerically simulated data for an example field source device.
Figure 4B:
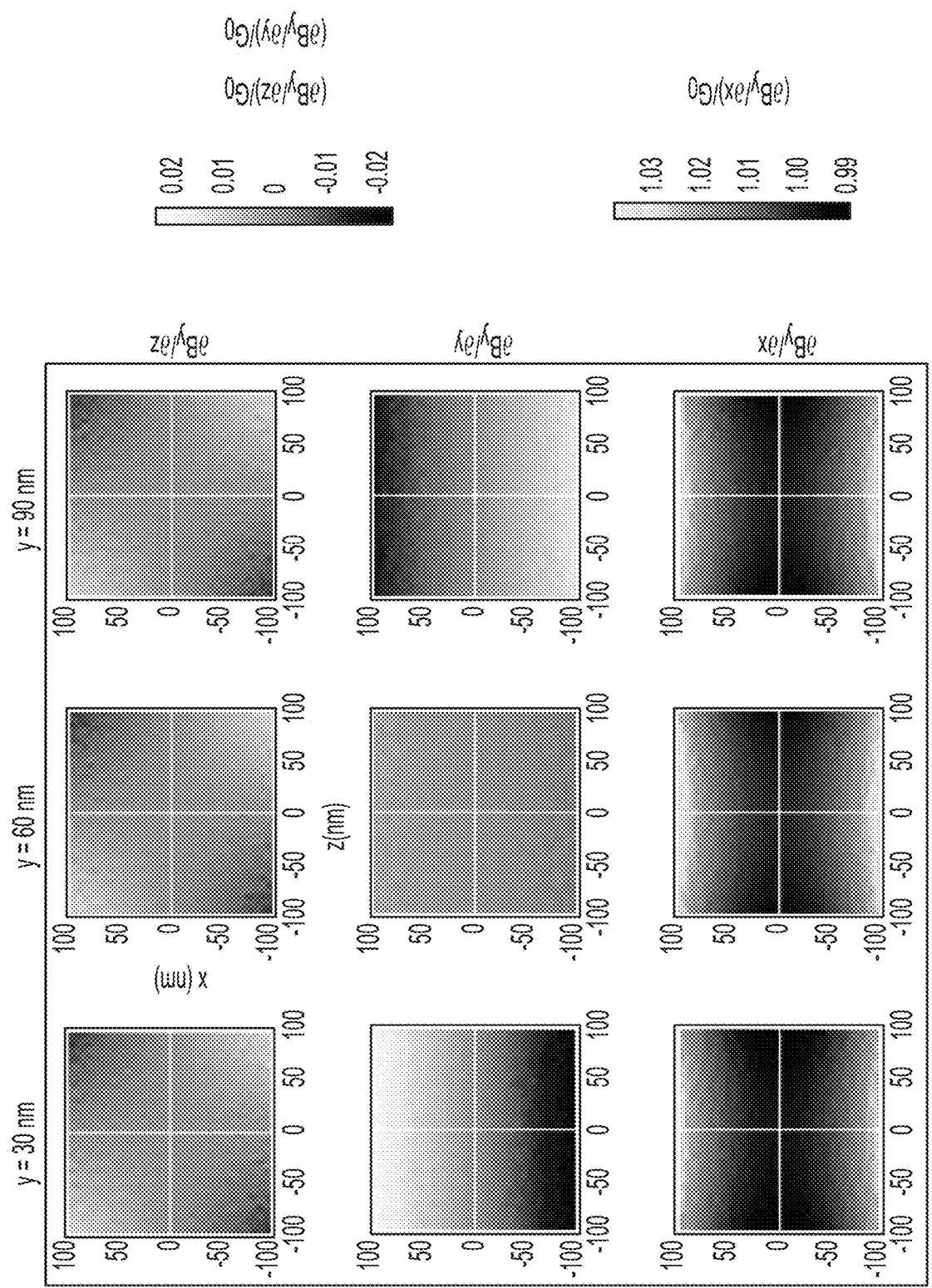
Figure 4C:
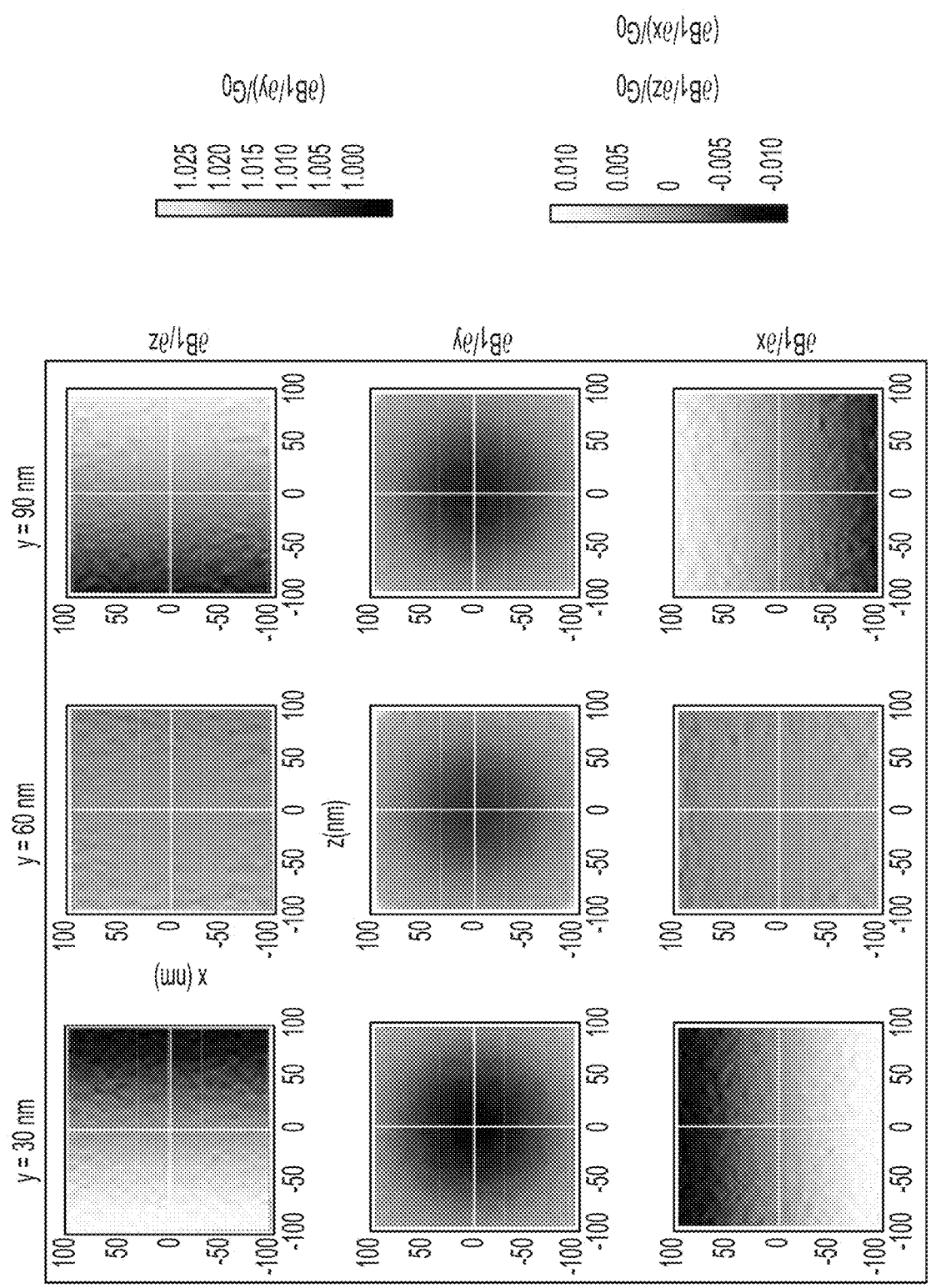

The magnetic field gradients that are applied to produce the coherent spatial encoding can include linear magnetic field gradients, which are magnetic fields that vary linearly with displacement over a spatial dimension. For example, linear magnetic field gradients can be generated over three mutually-orthogonal spatial dimensions to generate the coherent spatial encoding. In some cases, one or more of the linear magnetic field gradients rotates about an axis over time. For example, the example field source devices 200, 300 can generate linear magnetic field gradients that vary linearly over the x-direction, y-direction and z-direction; the linear magnetic field gradients over the x-direction and z-direction are static magnetic fields, and the linear magnetic field gradient over the y-direction is a rotating magnetic field that rotates about the y-axis over time. FIGS. 4A, 4B, and 4C show examples of the linear magnetic field gradients that can be produced by the example field source device 200 shown in FIGS. 2A, 2B, 2C, 2D, 2E, 2F, 2G to generate a coherent spatial encoding of spins. Other types of linear magnetic field gradients can be used to produce a coherent spatial encoding of spins in a magnetic resonance sample.

The coherent spatial encoding of spins generated by the linear magnetic field gradients can be described by an encoding wavenumber k. In some examples, the encoding wavenumber can be expressed in the form:

$$k = \gamma \tau_x G_x \hat{x} + \gamma \tau_y G_y \hat{y} + \gamma \tau_z G_z \hat{z}$$

where, $\gamma$ is the gyromagnetic ratio of the spins, $\tau_i$ are the respective encoding times (the duration of the gradient filed in the respective dimension), and $G_i = \partial B / \partial x_i$ are the respective components of the magnetic field gradient. Depending on the type of encoding being done, the magnetic field B may refer to a stationary lab field or a rotating field.

After the magnetic field gradients are used to produce the phase encoding, the ensemble magnetization can be measured, for example, when the spins are rotated back to the direction of the static field (e.g., by applying a reverse gradient sequence). In some examples, the measured spin signal is proportional to the normalized structure function, which may be represented as follows:

$$S(k) = \frac{1}{N_1 N_2 N_3} \sum_{n_1=1}^{N_1} \sum_{n_2=1}^{N_2} \sum_{n_3=1}^{N_3} \cos(k \cdot R)$$

where, $N_i$ are the number of atoms in the measurement ensemble, and k is the encoding wavenumber. In some implementations, for the structure function to be nonzero, the following condition may be necessary, $k \cdot a_i = 2\pi e_i$, where $e_i \in \mathbb{Z}$. are the diffraction orders. To measure the set {a}, a minimum of three separate measurements may be necessary, with the encoding vector for each measurement being:

$$k_i = 2\pi \hat{a}_i / a_1$$

where, $a_i = a_i \hat{a}_i$. If the above equation is satisfied, then all the spins contribute coherently, and the structure function is $S(k_i)=1$.

Accordingly, an appropriate encoding wavenumber k can be generated to obtain an NMR measurement on a size scale equal to the displacement vector R. For instance, the encoding wavenumber k of the spatial encoding generated over the magnetic resonance sample can define the spatial resolution of measurements that can be obtained from the magnetic resonance sample based on the spatial encoding. In some cases, the atomic-scale features of a sample can be observed from a magnetic resonance sample when the encoding wavenumber is large enough to resolve atomic-scale distances in a magnetic resonance measurement. For example, when $1/\|k\|$ is on the order of Angstroms (Å), an atomic-scale magnetic resonance diffraction measurement may be obtained, and the atomic-scale magnetic resonance diffraction measurement can be used to analyze atomic structure of the sample.

In some instances, the field source device 200 shown in FIGS. 2A-2G, or the field source device 300 shown in FIGS. 3A-3B can generate magnetic field gradients of sufficiently high magnitude and linearity to achieve atomic-scale nuclear magnetic resonance (NMR) resolution. To achieve a coherent spatial encoding with atomic-scale resolution, the field source device can apply magnetic field gradients having field strengths of $G=1/(\gamma \tau a)$, where $\gamma$ is the spin gyromagnetic ratio, $\tau$ is the time that the spin coherence evolves in the gradient, and a is the spacing between spins. The coherent spatial encoding may extend over a significant volume of the sample, for example, a volume of spins having a smallest spatial dimension greater than 40 nanometers (nm)

To generate a coherent spatial encoding of spins, it is often useful to use magnetic field gradients that have highly linear variation, that is $\partial B''/\partial x_i^n = 0$, $\forall n > 1$. Higher order variations of the magnetic field will in general degrade the diffraction signal. In some examples, this problem can be controlled using optimal control theory. In other examples, this may be addressed solely based on the linear field profile to encode spins.

Figure 6:
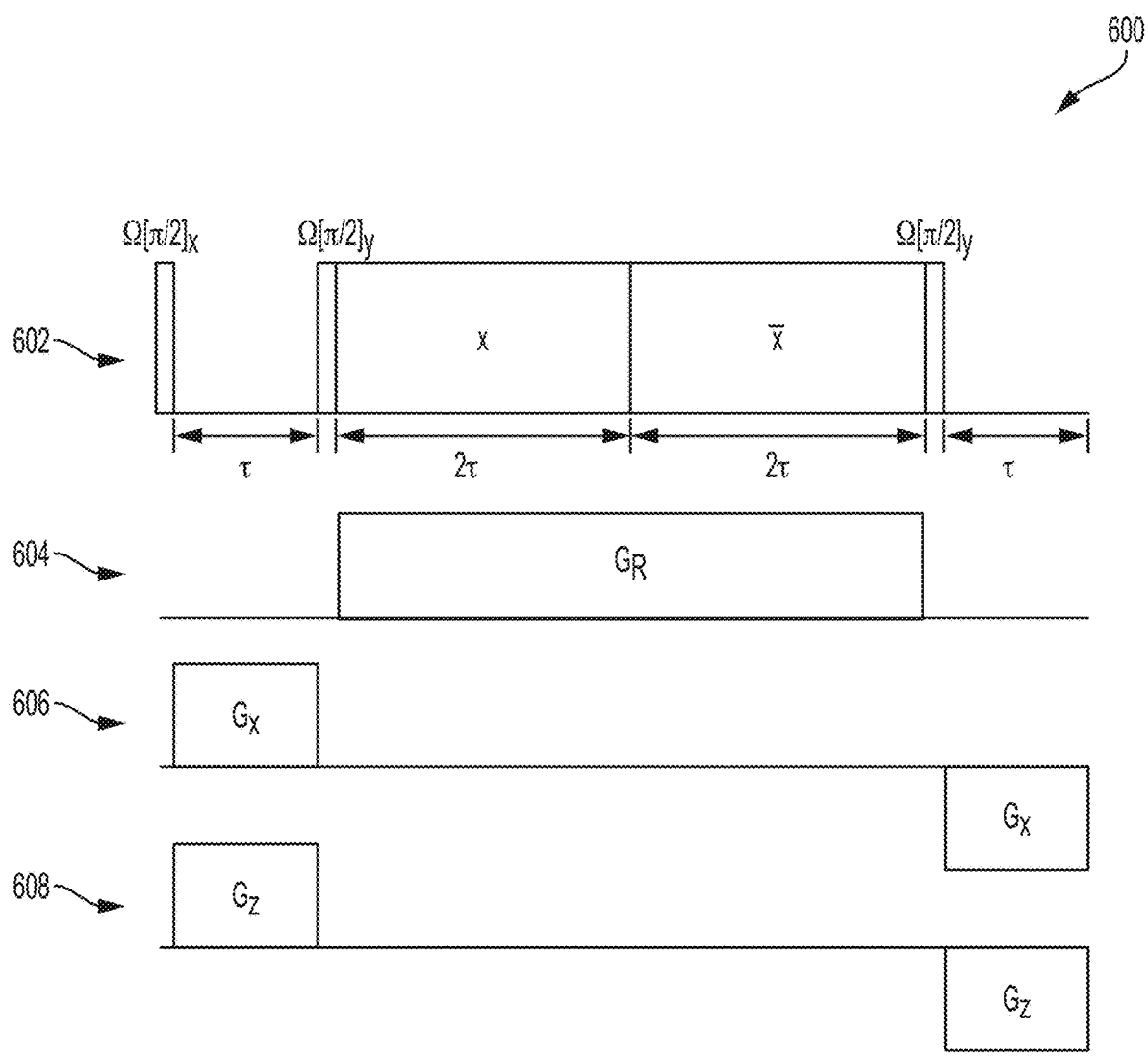
FIG. 6 shows an example pulse sequence that may be applied using a field source device.

In some implementations, the magnetic field control sequence that generates the coherent spatial encoding over the spins can include a pulse sequence that generates radio-frequency fields that dynamically decouple the spins. For example, the dynamical decoupling may be performed using a magic echo pulse sequence. An example of a magic echo pulse sequence is shown in FIG. 6. Another type of dynamical decoupling technique may be used in some cases.

In the following discussion, atomic-scale NMR diffraction using the example field source device 200 in FIGS. 2A, 2B, 2C, 2D, 2E, 2F and 2G is demonstrated using numerical simulations. To calculate the diffraction signal in a numerical simulation, a 3D lattice of spins may be assumed and the structure function may be calculated using the above equations. In one example, a $^{31}$P-lattice in an InP nanowire (InPNW) may be imaged. For these measurements, a few-μm long InPNW is attached to the tip of the SiNW, and the expected force signal from the P-lattice may be calculated.

The InPNWs may be grown with a Wurtzite structure having lattice constants $\alpha=4.14$ Å, and $c=6.8$ Å. For the simulations described here, the spacing between successive layers is $c/2=3.4$ Å. The $^{31}$P nuclei are spin-1/2 nuclei, with a gyromagnetic ratio of $\gamma_p/2\pi = 17.235$ MHz/T and magnetic moment $\mu_p = 5.62 \times 10^{-27}$ J/T. The P-atoms may be encoded along the c-axis direction using the rf-field gradient. The c-axis may be assumed to be parallel to the y-direction in FIG. 2G. The encoding wavenumber may be represented as $k(\tau) = \gamma_p G_R \tau_R \hat{y}$. A full 3D field distribution may be used for calculations. A MAGGIC spin detection protocol, as shown in FIG. 6, may be used to detect the statistical imbalance of the longitudinal magnetization in the ensemble of spins located at the tip of the SiNW. The spin signal may be represented as follows:

$$F_z = \frac{1}{2} N(D_c \mu_p)^2 \left(\frac{\partial B_y}{\partial_z}\right)^2$$

where N is the number of spins in the detection volume, $D_c \approx 0.8$ is the duty cycle of the MAGGIC detection, and $\partial B_y/\partial_z$ is the component of the magnetic field gradient generated by the constriction 202 that produces a force on the SiNW in the z-direction (the direction of oscillation) from the longitudinal (y-component) spin magnetization.

In the numerical simulations described here, the magnetic resonance sample is a rectangular slab of InP positioned above the constriction 202 of the field source device. The longitudinal component of each P-spin may be evolved in the sample according to $\cos(\gamma_p B_1(r)\tau_R)$ to calculate the longitudinal magnetization after an encoding time $\tau_R$. Here, $B_1(r)$ is the rf field produced by the gradient wires inside the sample volume. The longitudinal magnetization may be weighted by $(\partial B_y(r)/\partial z)^2$ from the constriction 202. The quadratic gradient term may scale the contribution of each P-spin to the total force signal. The gradient readout may be modulated at a frequency near the mechanical resonance frequency of the SiNW, and is present only during the spin detection part of the measurement.

As described herein, diffraction measurements utilize three different components of the magnetic field gradient for phase encoding: $G_x = \partial B_y/\partial x$ and $G_z = \partial B_y/\partial z$ are gradients in the static external field, and $G_R = \partial B_1/\partial y$ is the gradient in the rf field. With reference to the coordinate system, a static principal magnetic field is applied in the y-direction. The magnetic field distribution is calculated in numerical simulations. Simulations are performed assuming stationary currents. This assumption is justified because for the typical rf frequencies used in these measurements, which range from 50-100 MHz, the size of the structure is much smaller than the wavelength of the electromagnetic fields. FIGS. 4A, 4B, and 4C show the magnetic field distribution near the constriction 202 produced by field source device 200. The calculations indicate that excellent field linearity can be achieved in the volume surrounding the constriction 202.

FIG. 4A includes a collection of plots demonstrating the magnetic fields produced by the field source device depicted in FIG. 2G, in various directions. In particular, the plots show three components of the $B_y$ magnetic field [$\partial B_y/\partial z$, $\partial B_y/\partial y, \partial B_y/\partial x$] in a 100 nm×100 nm region in the xz-plane produced by the depicted gradient wires over the center of the constriction 202. Distributions are calculated for the three surface heights indicated on the top row of each plot. The center of the constriction is located at (z=0, y=0, x=0). The fields are calculated for $I_x=200$ mA−pk. Each image is normalized to the gradient $G_0 = \partial B_y/\partial z(z=0, y=60$ nm, x=0), where $G_0 = -0.31$ G/nm.

FIG. 4B includes a collection of plots showing three components of the $B_y$ gradient [$\partial B_y/\partial z, \partial B_y/\partial y, \partial B_y/\partial x$] in a 100 nm×100 nm region in the xz-plane produced by the depicted gradient wires over the center of the constriction 202. Distributions are calculated for the three surface heights indicated on top of row of the plots. The center of the constriction is located at (z=0, y=0, x=0). The fields are calculated for $I_z$=200 mA–pk. Each image is normalized to the gradient $G_0 = \partial B_y/\partial x(z=0, y=60$ nm, $x=0)$, where $G_0 = -0.31$ G/nm.

FIG. 4C includes a collection of plots showing three components of the $B_1$ gradient [$\partial B_1/\partial z, \partial B_1/\partial y, \partial B_1/\partial x$] in a 100 nm×100 nm region in the xz-plane produced by the depicted gradient wires over the center of the constriction 202. Distributions are calculated for the three surface heights indicated on top of each row of plots. The center of the constriction is located at (z=0, y=0, x=0). The fields are calculated for $I_x$=200 mA–pk and $I_z$=200 mA–pk, for the modulation $I_R(t) = I_z \cos \omega_L t + I_x \sin \omega_L t$, where $\omega_L$ is the Larmor frequency. Each image is normalized to the gradient $G_0 = \partial B_1/\partial y(z=0, y=60$ nm, $x=0)$, where $G_0 = -0.31$ G/nm.

Figure 5A:
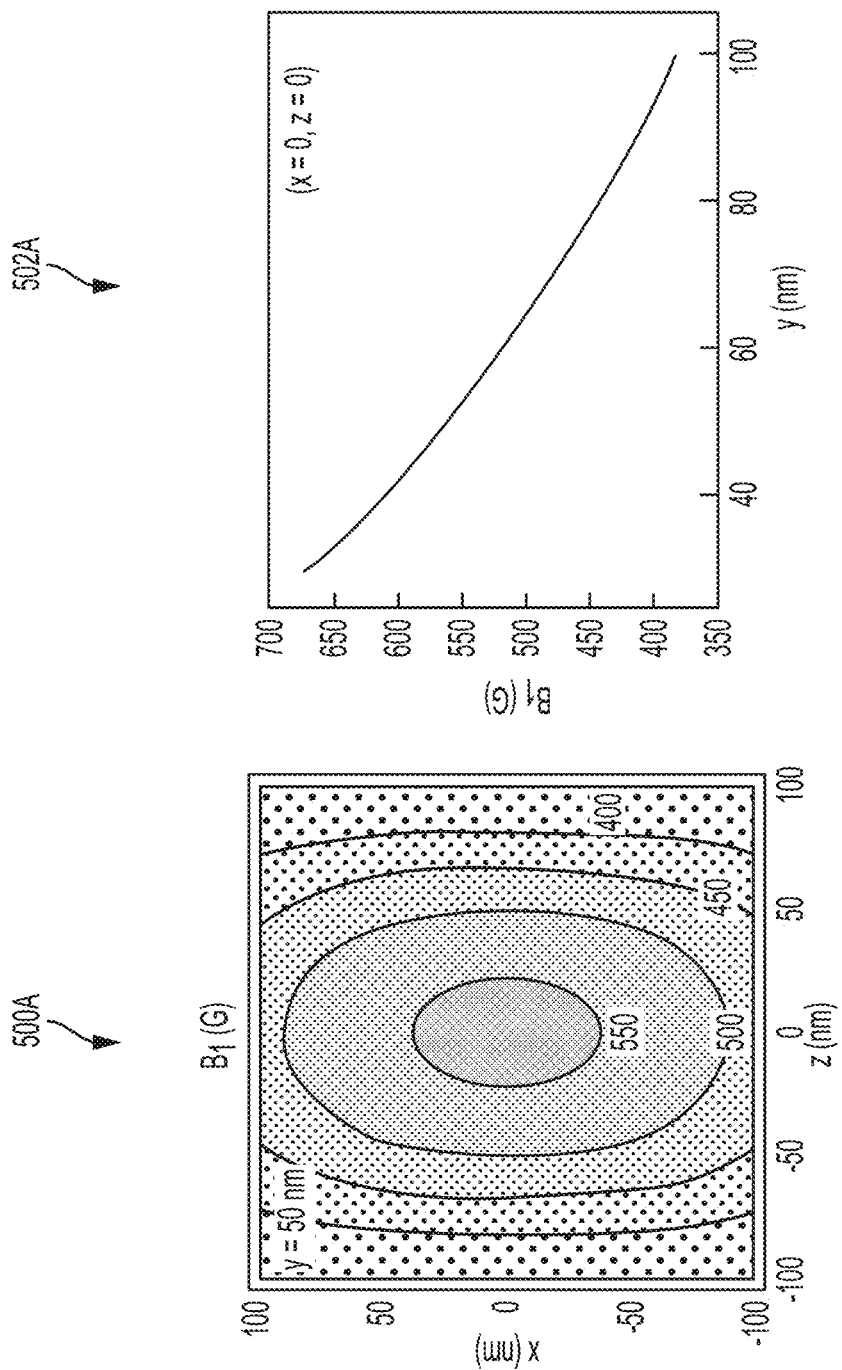
FIGS. 5A and 5B include a collection of plots showing numerically simulated data for an example field source device.
Figure 5B:
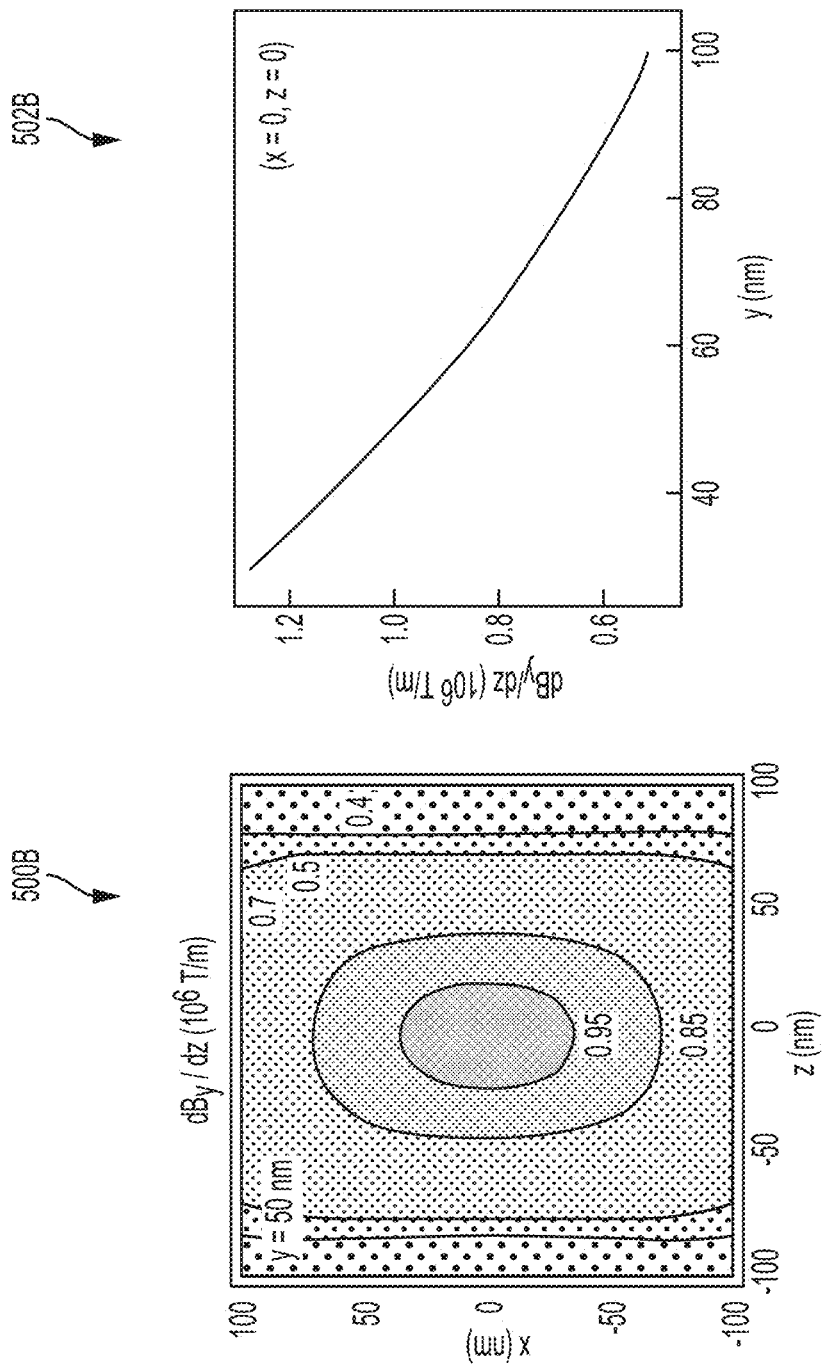

The fields from the constriction 202 may be used for implementing optimal control theory (OCT) unitary spin rotations, and for generating field gradients for spin readout. FIGS. 5A and 5B show examples of radio-frequency ($B_1$) fields and field gradients produced by the constriction 202. The geometry shown combines high field linearity important for phase encoding, and the ability to produce high amplitude radio-frequency pulses ($B_1$) fields and field gradients, which are important for high fidelity spin control and sensitive spin detection FIG. 6 shows an example pulse sequence 600 that may be applied using a field source device. For instance, the pulse sequence 600 may be applied to a magnetic resonance sample using the field source device 200 shown in FIGS. 2A-2G or another field source device to perform atomic-scale NMR diffraction. As shown in FIG. 6, the pulse sequence 600 includes a radio-frequency component 602, a rotating gradient component 604, an x-gradient component 606, and a z-gradient component 608. The pulse sequence 600 may include additional or different features and components.

The radio-frequency component 602 of the example pulse sequence 600 can be applied to the magnetic resonance sample by signals delivered to the constriction 202 of the example field source device 200. Here, the notation $\Omega[\pi/2]x$ refers to a $\pi/2$ rotation pulse about the x axis, optimized using an optimal control theory (OCT) process. Similarly, the notation $\Omega[\pi/2]y$ refers to a $\pi/2$ rotation pulse about the y-axis, optimized using an optimal control theory (OCT) process. An example of an optimal control theory (OCT) process that can be used to optimize radio-frequency pulses is the Gradient Ascent Pulse Engineering (GRAPE) method. Other types of OCT processes may be used. FIG. 5A shows an example of the radio-frequency magnetic fields produced by the constriction used to apply the OCT pulses.

The x-gradient component 606 of the example pulse sequence 600 can be applied to the magnetic resonance sample by signals delivered to a first pair of gradient coils on opposite sides of the magnetic resonance sample. The z-gradient component 608 of the example pulse sequence 600 can be applied to the magnetic resonance sample by signals delivered to a second pair of gradient coils on other opposite sides of the magnetic resonance sample. The x-gradient component 606 and the z-gradient component 608 represent linear magnetic field gradients that are applied in the lab frame.

The rotating gradient component 604 of the example pulse sequence 600 can be applied to the magnetic resonance sample by signals delivered to both pairs of gradient coils on all four sides of the magnetic resonance sample. The rotating gradient component 608 represents linear magnetic field gradients that are applied in the rotating frame.

Figure 7:
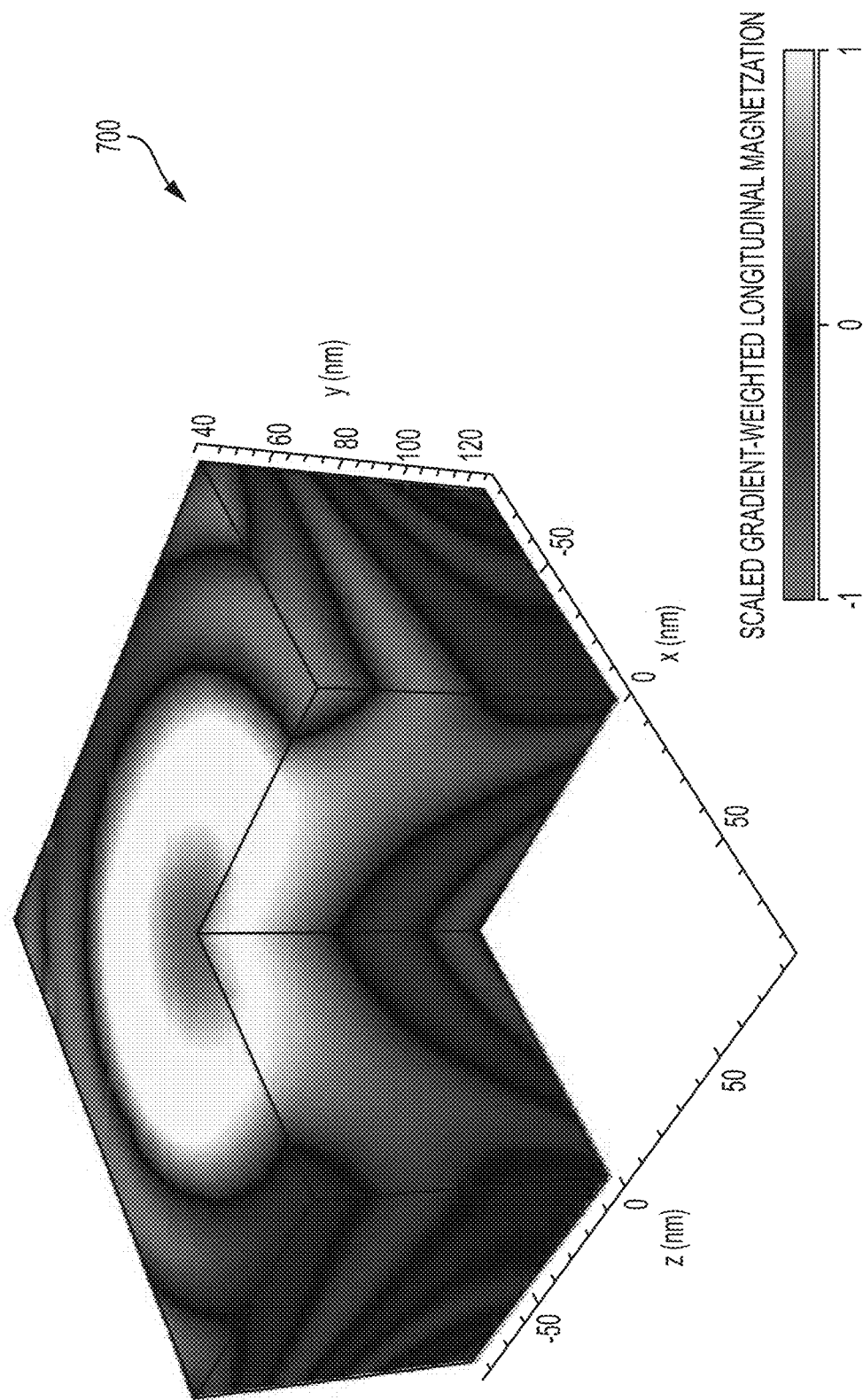
FIG. 7 includes a plot showing an example gradient-weighted longitudinal magnetization for an array.
Figure 8:
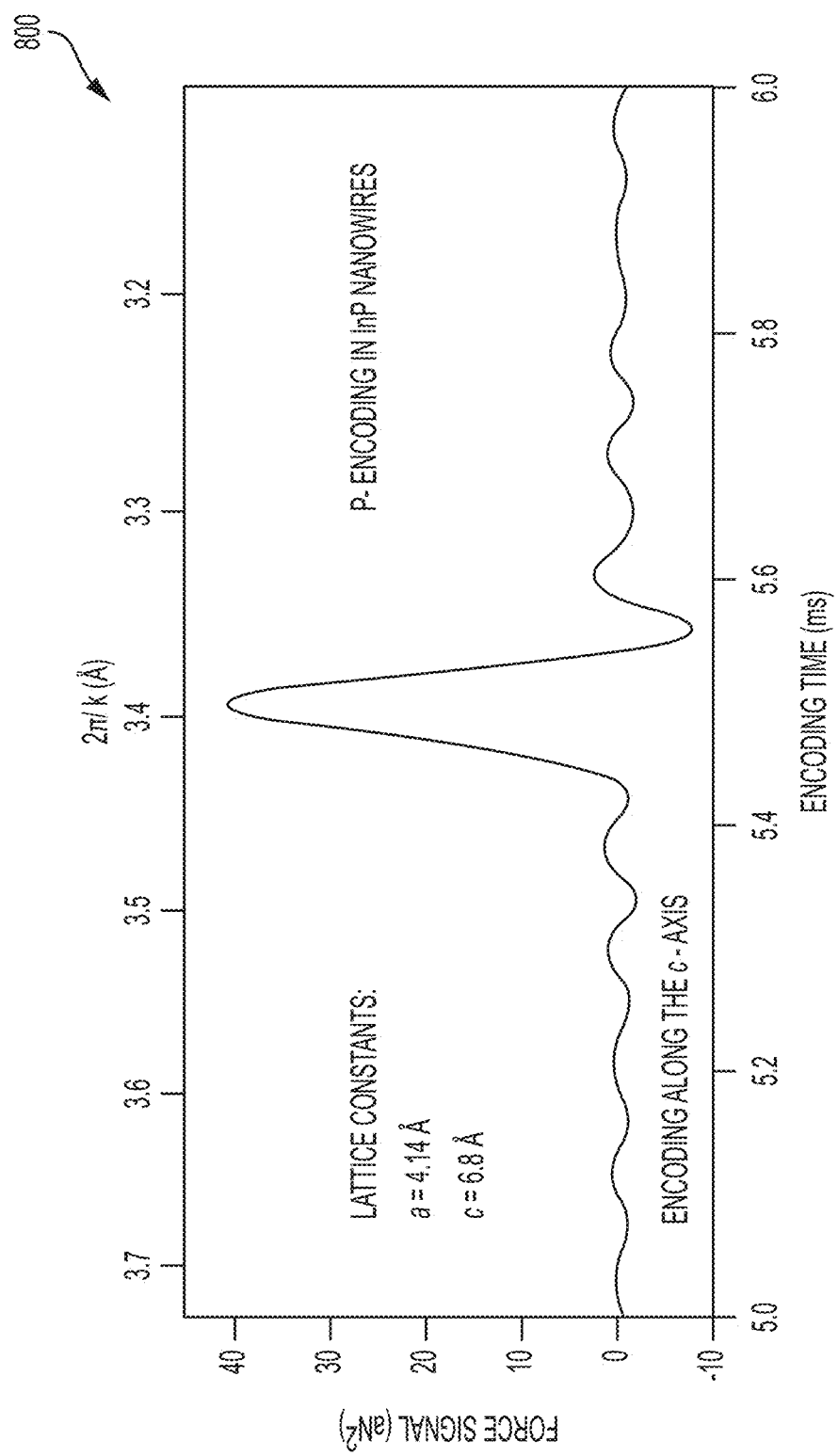
FIG. 8 includes a plot showing an example nuclear magnetic resonance (NMR) signal as a function of encoding time.

The magnetic resonance measurement signal that may be produced using the example pulse sequence 600 shown in FIG. 6 can be studied using numerical simulations. For instance, the total force may be calculated by summing up the contribution from each P-spin according to equations above. A plot of the total force as a function of encoding time is shown in FIG. 8. The light grey central region in FIG. 7 represents an ensemble of spins in roughly a 100-nm diameter×50-nm deep volume that contribute coherently to the spin signal. This large population of spins produces a significant signal that may be easily detected. In a similar manner the calculation may be extended to other spatial dimensions.

FIG. 7 shows a plot 700 of the gradient-weighted longitudinal magnetization for an array of size $N_a \times N_a \times N_c$ of P-atoms. This plot is associated with $N_a$=400 and $N_c$=250. Calculations assumed the magnetic resonance sample was centered with respect to the constriction 202, and positioned at a minimum separation (in the y-direction) of 40 nm with respect to the top surface of the constriction 202. The values of $B_1$ used for phase encoding are plotted in FIG. 4C. The greyscale indicates the normalized gradient-weighted magnetization. This particular image corresponds to the encoding time of $\tau_R$=5.50 ms, corresponding to the time when the peak diffraction signal forms. Note that that a coherent signal is produced by a large fraction of the sample that overlaps the region of space that experiences the high field gradients produced by the constriction 202. The readout gradient used for spin detection is shown in FIG. 5B.

FIG. 8 includes a plot depicting an NMR diffraction signal as a function of the encoding time $\tau_R$. The top axis is derived based on the discussions herein assuming the encoding gradient $G_R$=0.31 G/nm. The signal is calculated for a sample volume corresponding to $N_a$=400 and $N_c$=250 and a minimum sample separation of 40 nm with respect to the top surface of the constriction 202. The example data shown in FIG. 8 shows that the coherent spatial encoding generated over the P-spin ensemble produces NMR measurements having a spatial resolution that is less than 5 Angstroms (Å). For instance, as shown in FIG. 8, the NMR diffraction signal corresponds to a value of $2\pi/k$ in the range of 3.3 to 3.5 Å. Such a resolution corresponds to atomic-scale structures, and accordingly, the coherent spatial encoding can generate atomic-scale NMR diffraction measurements, which can be used to analyze atomic-scale features of the magnetic resonance sample.

In a general aspect, a field source device is configured for use in a magnetic resonance system.

In a first example, the field source device includes a substrate having a surface, and a conductor in a first layer on the surface of the substrate. The conductor includes two tapered portions that are tapered in opposite directions parallel to the surface of the substrate, and a constriction that connects respective narrow ends of the two tapered portions. The field source device further includes gradient coils in a second layer on the substrate, the gradient coils are spaced apart from the substrate. A thickness of the gradient coils is centered, in a direction perpendicular to the surface, above a maximum height of the constriction.

Implementations of the first example may include one or more of the following features. The gradient coils may include a first pair of gradient coils on first and second opposite sides of the constriction, and a second pair of gradient coils on third and fourth opposite sides of the constriction. The first pair of gradient coils may be configured to generate a first magnetic field gradient, in a sample region, along a first spatial dimension parallel to the surface; and the second pair of gradient coils may be configured to generate a second magnetic field gradient, in the sample region, along a second spatial dimension parallel to the surface. The constriction may be configured to generate a readout magnetic field gradient, in the sample region, along a third spatial dimension perpendicular to the surface.

Implementations of the first example may include one or more of the following features. The field source device may further include an insulating layer between the substrate and the second layer. The constriction may have a width in the range of 150 to 300 nanometers (nm). The maximum height of the constriction may be in the range of 100 to 200 nanometers (nm), and the thickness of the gradient coils may be centered more than 30 nanometers (nm) above the maximum height of the constriction.

In a second example, a magnetic resonance system includes a primary magnet system configured to generate a principal magnetic field in a sample region. The magnetic resonance system also includes a field source device. The field source includes a substrate, a first conductor layer on the substrate, and a second conductor layer on the substrate. The first conductor layer includes a constriction configured to generate a radio frequency magnetic field in the sample region. The second conductor layer is vertically centered above the first conductor layer, and includes gradient coils configured to generate first, second, and third magnetic field gradients along respective first, second and third mutually-orthogonal spatial dimensions in the sample region.

Implementations of the second example may include one or more of the following features. The magnetic resonance system may further include a control system operably connected to the field source device, wherein the gradient coils are configured to generate the respective magnetic field gradients based on control signals received from the control system. The magnetic resonance system may further include a mechanical resonator mechanically coupled to a sample in the sample region, and an optical system configured to detect vibration of the mechanical resonator. The first conductor layer may include two tapered portions that are tapered in opposite directions, and the constriction may connect respective narrow ends of the two tapered portions.

Implementations of the second example may include one or more of the following features. The gradient coils may be spaced apart from the substrate, and a thickness of the gradient coils may be vertically centered above a maximum height of the constriction. The magnetic resonance system may further include an insulating layer between the substrate and the second conductor layer. The gradient coils may be configured to generate the first, second, and third magnetic field gradients such that the first magnetic field gradient includes a static gradient that varies linearly along the first spatial dimension, the second magnetic field gradient includes a static gradient that varies linearly along the second spatial dimension, and the third magnetic field gradient includes a rotating gradient that varies linearly along the third spatial dimension.

In a third example, a magnetic resonance method includes applying a principal magnetic field to a sample, and applying a magnetic field control sequence to the sample. The magnetic field control sequence includes magnetic field gradients that generate a coherent spatial encoding of spins in the sample. The coherent spatial encoding may has a spatial resolution that is less than 5 Angstroms (Å). The method further includes obtaining a magnetic resonance measurement of the sample based on the coherent spatial encoding.

Implementations of the third example may include one or more of the following features. The sample may be mechanically coupled to a mechanical resonator. Obtaining the magnetic resonance measurement may further include applying to the sample a readout magnetic field gradient that interacts with the spins to induce vibration of the mechanical resonator, and detecting the vibration of the mechanical resonator. The mechanical resonator may include a silicon nanowire, and the vibration may be detected by a laser interferometer. The readout magnetic field gradient may be generated by passing current thorough a constriction in a field source device. The mechanical resonator may support the sample in a sample region.

Implementations of the third example may include one or more of the following features. The magnetic field gradients that generate the coherent spatial encoding may include a first static magnetic field gradient that varies linearly in the sample region along a first spatial dimension, a second static magnetic field gradient that varies linearly in the sample region along a second spatial dimension, and a rotating magnetic field gradient that varies linearly in the sample region along a third spatial dimension. The magnetic field control sequence may include radio-frequency fields configured to dynamically decouple the spins. The radio-frequency fields configured to dynamically decouple the spins may include a magic echo pulse sequence. The method may further include using optimal control theory to parameterize the radio-frequency fields. The coherent spatial encoding may extend over a volume having a smallest spatial dimension greater than 40 nanometers (nm).

In a fourth example, a magnetic resonance diffraction method includes applying a principal magnetic field to a sample, and applying a magnetic field control sequence to the sample. The magnetic field control sequence includes magnetic field gradients that generate a coherent spatial encoding of spins in the sample. The method further includes obtaining an atomic-scale magnetic resonance diffraction measurement of the sample based on the coherent spatial encoding, and using the atomic-scale magnetic resonance diffraction measurement to analyze atomic structure of the sample.

Implementations may include one or more of the following features. The coherent spatial encoding may have a spatial resolution that is less than 5 Angstroms (Å). The magnetic field gradients that generate the coherent spatial encoding may include a first static magnetic field gradient that varies linearly in the sample region along a first spatial dimension, a second static magnetic field gradient that varies linearly in the sample region along a second spatial dimension, and a rotating magnetic field gradient that varies linearly in the sample region along a third spatial dimension. The magnetic field control sequence may include radio-frequency fields configured to dynamically decouple the spins. The radio-frequency fields configured to dynamically decouple the spins may include a magic echo pulse sequence. The method may further include using optimal control theory to parameterize the radio-frequency fields. The coherent spatial encoding may extend over a volume having a smallest spatial dimension greater than 40 nanometers (nm).

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of embodiments have been described. Nevertheless, it will be understood that various modifications can be made. Accordingly, other embodiments are within the scope of the following claims.

What is claimed is:

1. A field source device configured for a magnetic resonance system, the field source device comprising:
    a substrate comprising a surface;
    a conductor in a first layer on the substrate, the conductor comprising:
        two tapered portions that are tapered in opposite directions parallel to the surface of the substrate; and
        a constriction that connects respective narrow ends of the two tapered portions;
    gradient coils in a second layer on the substrate, the gradient coils being spaced apart from the substrate, a thickness of the gradient coils being centered, in a direction perpendicular to the surface, above a maximum height of the constriction.

2. The field source device of claim 1, wherein the gradient coils comprise:
    a first pair of gradient coils on first and second opposite sides of the constriction; and
    a second pair of gradient coils on third and fourth opposite sides of the constriction.

3. The field source device of claim 2, wherein:
    the first pair of gradient coils are configured to generate a first magnetic field gradient, in a sample region, along a first spatial dimension parallel to the surface; and
    the second pair of gradient coils are configured to generate a second magnetic field gradient, in the sample region, along a second spatial dimension parallel to the surface.

4. The field source device of claim 3, wherein the constriction is configured to generate a readout magnetic field gradient, in the sample region, along a third spatial dimension perpendicular to the surface.

5. The field source device of claim 1, further comprising an insulating layer between the substrate and the second layer.

6. The field source device of claim 1, wherein the constriction has a width in the range of 150 to 300 nanometers (nm).

7. The field source device of claim 1, wherein the maximum height of the constriction is in the range of 100 to 200 nanometers (nm), and the thickness of the gradient coils is centered more than 30 nanometers (nm) above the maximum height of the constriction.

8. A magnetic resonance system comprising:
    a primary magnet system configured to generate a principal magnetic field in a sample region; and
    a field source device comprising:
        a substrate;
        a first conductor layer on the substrate and comprising a constriction configured to generate a radio frequency magnetic field in the sample region; and
        a second conductor layer on the substrate, vertically centered above the first conductor layer, and comprising gradient coils configured to generate first, second, and third magnetic field gradients along respective first, second and third mutually-orthogonal spatial dimensions in the sample region.

9. The magnetic resonance system of claim 8, comprising a control system operably connected to the field source device, wherein the gradient coils are configured to generate the respective magnetic field gradients based on control signals received from the control system.

10. The magnetic resonance system of claim 9, comprising:
    a mechanical resonator mechanically coupled to a sample in the sample region; and
    an optical system configured to detect vibration of the mechanical resonator.

11. The magnetic resonance system of claim 8, wherein the first conductor layer comprises two tapered portions that are tapered in opposite directions, and the constriction connects respective narrow ends of the two tapered portions.

12. The magnetic resonance system of claim 11, wherein the gradient coils are spaced apart from the substrate, and a thickness of the gradient coils is vertically centered above a maximum height of the constriction.

13. The magnetic resonance system of claim 12, comprising an insulating layer between the substrate and the second conductor layer.

14. The magnetic resonance system of claim 8, wherein the gradient coils are configured to generate the first, second, and third magnetic field gradients such that:
    the first magnetic field gradient comprises a static gradient that varies linearly along the first spatial dimension;
    the second magnetic field gradient comprises a static gradient that varies linearly along the second spatial dimension; and
    the third magnetic field gradient comprises a rotating gradient that varies linearly along the third spatial dimension.

15. A magnetic resonance method comprising:
    applying a principal magnetic field to a sample;
    applying a magnetic field control sequence to the sample, the magnetic field control sequence comprising magnetic field gradients that generate a coherent spatial encoding of spins in the sample, wherein the coherent spatial encoding has a spatial resolution that is less than 5 Angstroms (Å); and
    obtaining a magnetic resonance measurement of the sample based on the coherent spatial encoding.

16. The magnetic resonance method of claim 15, wherein the sample is mechanically coupled to a mechanical resonator, and obtaining the magnetic resonance measurement comprises:
    applying to the sample a readout magnetic field gradient that interacts with the spins to induce vibration of the mechanical resonator; and
    detecting the vibration of the mechanical resonator.

17. The magnetic resonance method of claim 16, wherein the mechanical resonator comprises a silicon nanowire, and the vibration is detected by a laser interferometer.

18. The magnetic resonance method of claim 16, wherein the readout magnetic field gradient is generated by passing current thorough a constriction in a field source device.

19. The magnetic resonance method of claim 18, wherein the mechanical resonator supports the sample in a sample region.

20. The magnetic resonance method of claim 15, wherein the magnetic field gradients that generate the coherent spatial encoding include:
   a first static magnetic field gradient that varies linearly in the sample region along a first spatial dimension;
   a second static magnetic field gradient that varies linearly in the sample region along a second spatial dimension; and
   a rotating magnetic field gradient that varies linearly in the sample region along a third spatial dimension.

21. The magnetic resonance method of claim 20, wherein the magnetic field control sequence comprises radio-frequency fields configured to dynamically decouple the spins.

22. The magnetic resonance method of claim 21, wherein the radio-frequency fields configured to dynamically decouple the spins include a magic echo pulse sequence.

23. The magnetic resonance method of claim 21, comprising using optimal control theory to parameterize the radio-frequency fields.

24. The magnetic resonance method of claim 15, wherein the coherent spatial encoding extends over a volume having a smallest spatial dimension greater than 40 nanometers (nm).

* * * * *